US010371652B2

(12) United States Patent
Mohebbi et al.

(10) Patent No.: US 10,371,652 B2
(45) Date of Patent: *Aug. 6, 2019

(54) PROCESS FOR ACCURATELY PROFILING FLUID DISTRIBUTION IN MULTI-LAYER ABSORBENT ARTICLES IN TWO AND THREE DIMENSIONS

(71) Applicant: The Procter & Gamble Company, Cincinnati, OH (US)

(72) Inventors: Behzad Mohebbi, Schwalbach am Taunus (DE); Jan Claussen, Wiesbaden (DE); Justyna Paradowska, Frankfurt am Main (DE); J Michael Bills, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 139 days.

This patent is subject to a terminal disclaimer.

(21) Appl. No.: 15/729,690

(22) Filed: Oct. 11, 2017

(65) Prior Publication Data

US 2018/0106737 A1    Apr. 19, 2018

Related U.S. Application Data

(60) Provisional application No. 62/408,125, filed on Oct. 14, 2016.

(51) Int. Cl.
| | | |
|---|---|---|
| *G01N 24/08* | (2006.01) | |
| *A61F 13/84* | (2006.01) | |
| *G01R 33/30* | (2006.01) | |
| *A61F 13/42* | (2006.01) | |
| *G01R 33/28* | (2006.01) | |
| *G01R 33/44* | (2006.01) | |

(52) U.S. Cl.
CPC ............ *G01N 24/08* (2013.01); *A61F 13/42* (2013.01); *A61F 13/84* (2013.01); *G01R 33/30* (2013.01); *A61F 2013/8491* (2013.01); *G01R 33/281* (2013.01); *G01R 33/448* (2013.01)

(58) Field of Classification Search
None
See application file for complete search history.

(56) References Cited

U.S. PATENT DOCUMENTS

| | | | |
|---|---|---|---|
| 7,358,734 B2 | 4/2008 | Blümich et al. | |
| 7,391,215 B2 | 6/2008 | Callaghan et al. | |
| 9,964,501 B2 * | 5/2018 | Taicher | G01N 24/08 |
| 2014/0225611 A1 * | 8/2014 | Rapoport | G01R 33/3802 |
| | | | 324/309 |

(Continued)

OTHER PUBLICATIONS

Oligschläger, D., et al., Miniature mobile NMR sensors for material testing and moisture-monitoring, diffusion-fundamentals.org—The Open-Access Journal for the Basic Principles of Diffusion Theory, Experiment and Application, vol. 22(8), pp. 1-25 (2014).

(Continued)

*Primary Examiner* — Jermele M Hollington
*Assistant Examiner* — Douglas X Rodriguez
(74) *Attorney, Agent, or Firm* — Andrew J. Hagerty; Sarah M. DeCristofaro

(57) ABSTRACT

A process for profiling fluid distribution and analyzing fluid redistribution kinetics in multi-layer absorbent articles is disclosed.

17 Claims, 23 Drawing Sheets

(56) References Cited

U.S. PATENT DOCUMENTS

2015/0130463 A1* 5/2015 Wellman ................ G01N 24/08
324/321

OTHER PUBLICATIONS

Oligschläger, D., et al., Moisture dynamics in wall paintings monitored by single-sided NMR, Magnetic Resonance in Chemistry (MRC), vol. 53, pp. 48-57 (2015).

Vuong, Q. L., et al., Paramagnetic nanoparticles at potential MRI contrast agents: characterization, NMR relaxation, simulations and theory, Magnetic Resonance Mater Phy, vol. 25, pp. 467-478 (2012).

* cited by examiner

PROCESS FOR ACCURATELY PROFILING FLUID DISTRIBUTION IN MULTI-LAYER ABSORBENT ARTICLES IN TWO AND THREE DIMENSIONS

This application claims the benefit of U.S. Provisional Application No. 62/408,125 filed on Oct. 14, 2016, the entirety of which is incorporated by reference herein.

FIELD OF THE INVENTION

The present disclosure generally relates to measuring and profiling the two- and three-dimensional quantitative distribution of fluids in absorbent articles. More particularly, the present disclosure relates to a process using nuclear magnetic resonance (NMR) apparatus and a suitable contrast agent that can develop a better two- and three-dimensional profile of the fluid distribution through a multi-layer absorbent article such as a diaper or a catamenial device. Additionally, the present disclosure relates to a device incorporating a nuclear magnetic resonance (NMR) apparatus that can measure and analyze at least a two-dimensional profile of the fluid distribution in an absorbent article such as a diaper or a catamenial device as well as the components forming such absorbent articles.

BACKGROUND OF THE INVENTION

The liquid distribution and the kinetics of liquid redistribution is vital information that can be used to compare the functionality of different absorbent articles, such as hygiene products, and to develop new products. Currently, several techniques such as X-Ray and MRI are utilized to characterize the 3D liquid distribution within hygiene products. However, there is currently no known process to provide a fast data acquisition process in combination with a high resolution process at low cost to follow the kinetics of fluid movement inside absorbent articles.

NMR is a physical phenomenon based on the principle of exciting nuclear spins with radiofrequency pulses, the frequency of which matches the Larmor frequency of the nuclear spins. In other words, NMR is based on the nuclear magnetic properties of certain elements and isotopes of those elements. It is based on the principle that nuclei with a non-zero spin will have a magnetic dipole and therefore will interact with electromagnetic (EM) radiation.

This principle has been applied in many different research fields such as chemical structure analysis, materials testing and in medicine. To access certain nuclear spins via radiofrequency pulses, the nuclei have to be exposed to a magnetic field. These magnetic fields can be classified as high and low. Low magnetic fields as created by permanent magnets can yield magnetic field strengths up to 85 MHz proton Larmor frequency, whereas superconducting high field magnets reach drastically higher field strengths. Magnetic fields can either be produced by electrical currents running through cryogenically cooled coils of superconducting wires without resistance or by the use of permanent magnets.

The presence or absence of a spin and the nature of this spin is expressed in terms of the spin quantum number of the nucleus, which may either be 0, ½ or multiples of ½. In a uniform magnetic field a nucleus having a spin quantum number of ½ may assume two orientations relative to the applied magnetic field. The two orientations have different energies so that it is possible to induce a nuclear transition by the application of electromagnetic radiation of the appropriate frequency. This transition is resonance. Resonance arises when the correct combination of magnetic field strength and exciting frequency characteristics of the nuclei of interest are applied.

After resonance is achieved the NMR instrument records a signal, the signal being a function of the nature and amount of excited nuclei within the test sample as well as nuclear magnetic relaxation considerations. A NMR device generally comprises one or more magnets producing a strong homogenous field in combination with gradients within a test region to be applied for imaging, spectroscopy or relaxometry. The size and complexity of NMR spectrometers are largely a function of the magnetic field requirements. In contrast to NMR applications requiring homogenous magnetic fields, single sided, or open, NMR devices make use of inhomogeneous magnetic fields having highly uniform gradients.

One particular early form of single sided NMR, the NMR-Mobile Universal Surface Explorer (NMR-MOUSE) was introduced in 1995. The early design of the NMR-MOUSE was limited to a maximum penetration depth of less than 5 mm, and a depth profile resolution of only about a millimeter due to its U-Shape formed magnet. To achieve a flat, sensitive NMR volume at a greater distance removed from the magnet surface with a higher depth resolution a new magnet design was developed.

The new magnet design provided a magnetic assembly for an NMR apparatus, including a plurality of primary permanent magnets disposed in an array about an axis (hereafter "longitudinal axis"), the arrangement and/or characteristics of the plurality of magnets being such so as to create a zone of homogeneous magnetic field at some location along the axis forward of the array (and into the material when provided). The assembly can include a secondary permanent magnet located along the longitudinal axis, at least partly within the array of primary magnets.

As shown in FIG. 1, an exemplary prior art NMR-MOUSE 1005 provides a portable open NMR sensor equipped with a permanent magnet geometry that generates a highly uniform gradient perpendicular to the scanner surface. A frame 1007 with horizontal plane 1006 supports the specimen and remains stationary during the test. A flat sensitive volume of the specimen is excited and detected by a surface RF coil 1012 placed on top of the magnet 1010 at a position that defines the maximum penetration depth into the specimen. By repositioning the sensitive slice across the specimen by means of a high precision lift 1008, the scanner can produce one-dimensional profiles of the specimen's structure with high spatial resolution. If necessary the depth can be adjusted using the spacer 1011.

FIG. 2 shows an exemplary absorbent article specimen 1000 prepared for use with the exemplary prior art NMR-MOUSE 1005. The garment facing side of the specimen 1003 is mounted on a 50 mm×50 mm×0.30 mm glass slide 1001 using a 40.0 mm by 40.0 mm piece of double-sided tape 1002 (tape must be suitable to provide NMR signal amplitude). A top cap 1004 is prepared by adhering two 50 mm×50 mm×0.30 mm glass slides 1001 together using a 40 mm by 40 mm piece of two-sided tape 1002. The cap is then placed on top of the specimen. The two tape layers are used as functional markers to define the dimension of the specimen by the instrument. As can be understood, the prior art absorbent article system does not easily allow for the analysis of absorbent articles that expand. Additionally, a typical RF pulse sequence used in prior art NMR devices, such as the NMR-MOUSE system, is the Carr-Purcell-Meiboom-Gill (CPMG) pulse train. A pulse sequence is a visual representation of the pulses and delays used in a NMR experiment. A pulse is a collection of oscillating waves with a broad range of frequencies used to rotate the bulk magnetization. Most pulse sequences have more than one pulse which can help for signal enhancement and measuring relaxation times by separation of NMR interactions.

One of skill in the art will recognize that the deterioration of an NMR signal is analyzed in terms of two separate processes, each with their own time constants. One process, associated with $T_1$, is responsible for the loss of signal intensity. The other process, associated with $T_2$, is responsible for the broadening of the signal. Two distinguishable relaxation times in NMR are the longitudinal relaxation with a characteristic time, $T_1$, which is also known as Spin-Lattice relaxation, and transverse relaxation with a characteristic time, $T_2$, which is also known as Spin-Spin relaxation. The longitudinal relaxation is the time needed for magnetization in z direction to build up and reach an equilibrium state again ($M_{eq}$). The build-up rate of magnetization in z direction is proportional to its deviation from the thermal equilibrium state. Transverse relaxation corresponds to the loss of magnetization in the transverse plan. Stated more formally, $T_1$ is the time constant for the physical processes responsible for the relaxation of the components of the nuclear spin magnetization vector M parallel to the external magnetic field, $B_0$ (which is conventionally oriented along the z axis). $T_2$ relaxation affects the components of M perpendicular to $B_0$. In conventional NMR spectroscopy $T_1$ determines the recycle time, the rate at which an NMR spectrum can be acquired. Values of $T_1$ range from milliseconds to several seconds.

Due to the inhomogeneous static field generated by the open geometry of the profile NMR MOUSE, the free induction decay (FID) (i.e., the observable NMR signal generated by non-equilibrium nuclear spin magnetization processing about the magnetic field) is too short and not detectable. In order to overcome this problem, the CPMG pulse sequence is the most frequently used with single-sided NMR. The CPMG pulse sequence generally consists of a 90° pulse followed by 180° pulses that create a train of spin echoes. This sequence acts to refocus, or regain signal loss due to $B_0$ field inhomogeneity. The initial amplitude of the decay can be related to spin density, while the effective relaxation time $T_{2,eff}$ can be extracted by fitting an exponential function to the signal decay.

An exemplary prior art NMR-MOUSE is the Profile NMR-MOUSE model PM25 with High-Precision Lift available from Magritek Inc., San Diego, Calif. Exemplary requirements for the NMR-MOUSE are a nominal 50-100 μm resolution in the z-direction, a measuring frequency of 13.5 MHz, a maximum measuring depth of 25 mm, a static gradient of 8 T/m, and a sensitive volume (x-y dimension) of 40 mm by 40 mm.

However, several problems exist with the prior art NMR-MOUSE device. First, it was found that the prior art NMR-MOUSE system has revealed that a suitable CPMG sequence may require a repetition time of at least $5T_1$ to enable quantification of liquids. A given CPMG sequence quantification of liquid inside hygiene materials is not possible as $T_1$ varies over several magnitudes as a function of saturation and existence of bounded liquid. Additionally, published CPMG pulse sequences cannot be used for the fast quantification inside hygiene products and materials as the relaxation times $T_1$ and $T_2$ are strongly depending on the hygiene materials (such as foams, super absorber, pulp, nonwovens, etc.). To enable a fast quantification of liquids in hygiene materials and products, a CPMG pulse sequence in combination with the use of a contrast agent that can make the $T_1$ and $T_2$ times independent of the hygiene materials and their saturation levels is applied.

Second, the current NMR-MOUSE equipment is not suitable for measuring kinetics at a certain position in absorbent articles that have expansive properties as the region of interest generally swells out of the field of view. For example, a typical absorbent article, a diaper, will expand when an insult is applied to the surface and the insult migrates inward and is absorbed by the constituents forming the absorbent article. This is similar to the observed swelling of a sponge when it the surface is insulted by a fluid. The fluid migrates into the sponge and the sponge swells.

Thus, when measuring the characteristics of swellable objects, such as absorbent articles (diapers, catamenials, etc.) the expansion of the object and ensuing migration of the insulted surface away from the surface of the NMR prevents the observation and analysis of fluid migration into the absorbent article as point of reference (e.g., the insulted surface) having the fluid disposed thereon migrates away from the NMR surface.

Therefore, a need exists and it would be beneficial to provide a new device that can enhance the ability of low-field NMR devices to monitor and evaluate the fluid migration of fluids into an absorbent article by maintaining the point of reference at a fixed location relative to the NMR. In other words, there is a need for a test method that can be used for different absorbent articles to analyze liquid distribution and the kinetics of fluid redistribution within a layered structure. Such a process can improve the ability to map fluid migration through an absorbent article necessary to enhance the development of better quality absorbent articles as well as the materials used to manufacture absorbent articles. This need could include a method that provides for fast data acquisition (e.g., repetition time <250 ms) and high resolution in order to follow liquid migration inside an absorbent article. Such a process can be optimized to be used for different materials.

It is believed that the process also provide for fast quantification of fluid distribution by using a contrast agent in combination with an optimized CPMG pulse sequence with a short echo time and low numbers of echoes. Additionally, such a process should provide for a calibration procedure that can accurately determine the actual volume values of liquids applied to the absorbent article.

Additionally, it can be useful to provide markers suitable for use in profiling measurements can be recognized easily and help to detect the sample positioning.

SUMMARY OF THE INVENTION

The present disclosure provides for a process for quantification of fluid distribution and kinetics in multi-layer absorbent articles. The process comprises the steps of: a) providing a device comprising a frame, a pressure chamber, and an NMR sensor, the pressure chamber comprising a bladder assembly and a top plate disposed adjacent thereto, the bladder assembly and the top plate being separable; b) providing a first multi-layer absorbent article, the first multi-layer absorbent article having a top sheet and an absorbent core, the top sheet and the absorbent core comprising nuclei having excitable nuclear spins excited by radiofrequency pulses emitted by the NMR sensor; c) positioning the first multi-layer absorbent article between the bladder assembly and the top plate, the top sheet of the first multi-layer absorbent article being disposed within the pressure chamber so the absorbent core is disposed proximate to and in contacting engagement with the bladder assembly and the top sheet is disposed proximate to and in contacting engagement with the top plate when the bladder assembly and the top plate of the pressure chamber are conjoined; d) disposing the NMR sensor at a first position relative to the top plate and the top sheet contactingly engaged thereto; e) emitting the radiofrequency pulses from the NMR sensor to define a float sensitive volume of the first multi-layer absorbent article at the first position; f) detecting at least a portion of the nuclei having a non-zero spin interacting with the radiofrequency pulses at the first position; and, g) producing the fluid distribution profile of the first multi-layer absorbent article according to the detected nuclei having a non-zero spin interacting with the radiofrequency pulses at the first position.

The present disclosure also provides for a process for the analysis of the fluid redistribution kinetics in multi-layer absorbent articles. The process comprises the steps of: a) providing a device comprising a frame, a pressure chamber, and an NMR sensor, the pressure chamber comprising a conformable surface and a top plate disposed adjacent thereto, the bladder assembly and the top plate being separable; b) providing a first multi-layer absorbent article, the first multi-layer absorbent article having a top sheet and an absorbent core, the top sheet and the absorbent core comprising nuclei having excitable nuclear spins excited by radiofrequency pulses emitted by the NMR sensor; c) positioning the first multi-layer absorbent article between the conformable surface and the top plate, the top sheet of the first multi-layer absorbent article being disposed within the pressure chamber so the absorbent core is disposed proximate to and in contacting engagement with the conformable surface and the top sheet is disposed proximate to and in contacting engagement with the top plate when the conformable surface and the top plate of the pressure chamber are conjoined; d) disposing the NMR sensor at a first position relative to the top plate and the top sheet contactingly engaged thereto; e) insulting the top sheet of the first multi-layer absorbent article with at least a first fluid, the first fluid further comprising a contrast agent; f) emitting the radiofrequency pulses from the NMR sensor to define a float sensitive volume of the first multi-layer absorbent article at the first position; g) detecting at least a portion of the nuclei having a non-zero spin interacting with the radiofrequency pulses at the first position; and, h) analyzing said fluid redistribution kinetics of the first multi-layer absorbent article according to the detected nuclei having a non-zero spin interacting with the radiofrequency pulses at the first position.

DETAILED DESCRIPTION

Figure 1:
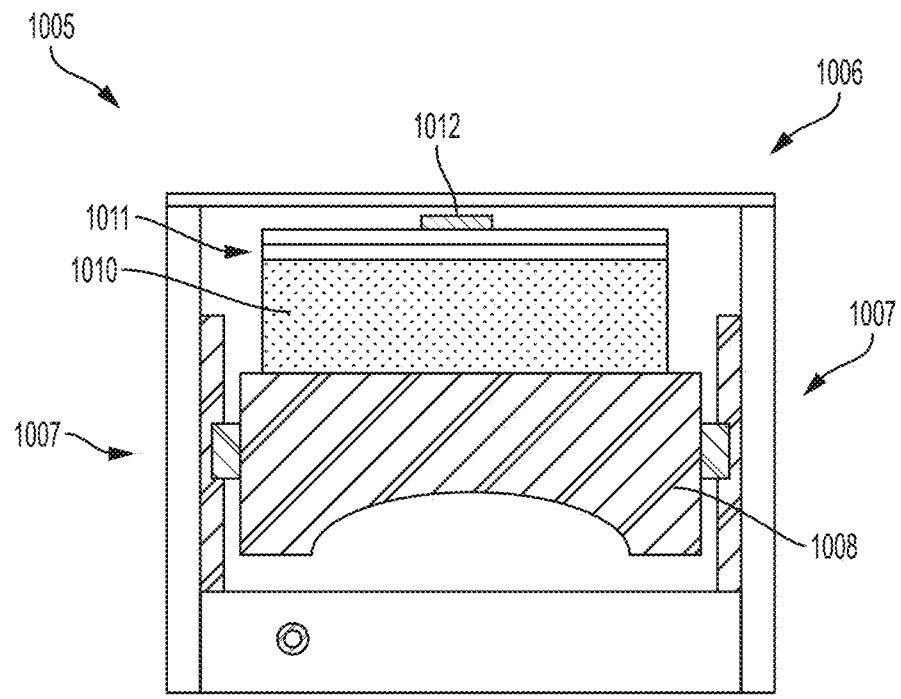
FIG. 1 is a cross-sectional view of an exemplary prior art NMR-MOUSE apparatus.
Figure 2:
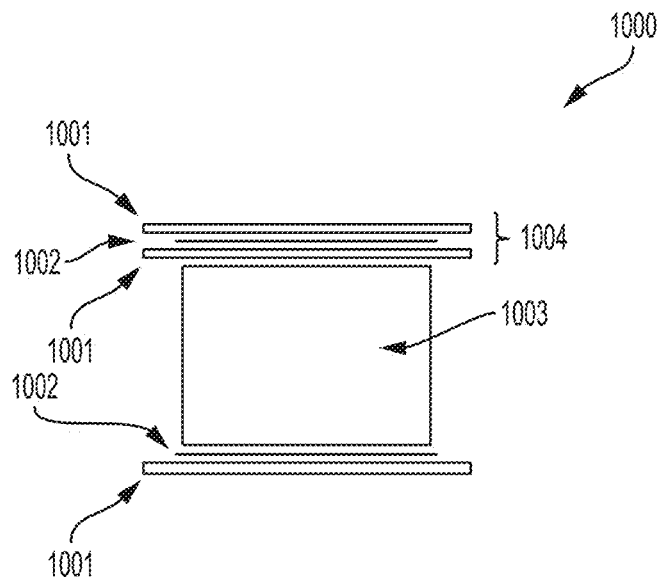
FIG. 2 is a cross-sectional view of an exemplary sample prepared for analysis by the exemplary prior art NMR-MOUSE shown in FIG. 1, the exemplary sample being disposable upon the sample surface of the NMR-MOUSE.

As used herein, the term "machine direction" (MD) refers to that direction which is parallel to the flow of the component materials used for the formation of absorbent articles through manufacturing equipment. The "cross-machine direction" (CD) is perpendicular to and co-planar with the machine direction. The "Z-direction" refers to that direction that is orthogonal to both the MD and CD.

As used herein, an "absorbent article" or "absorbent articles" refers to articles that absorb any type of fluid. These articles are typically disposable and generally includes paper towels, wipes, toilet paper, facial tissue, absorbent hygienic articles such as diapers and catamenial devices, absorbent articles used in the medical field such as wound dressings and surgical articles, absorbent articles used in food technology and conservation (such as fluid pads for meat, fish and the like), absorbent articles used industrially to absorb fluids, for example to contain spillage of chemicals in fluid form and absorbent hygienic articles, as well as the components of such exemplary absorbent articles which in and of themselves may also be absorbent.

One of skill in the art will understand that it would be desirable to develop a test method that can be used to quantify the liquid distribution and kinetics inside different materials and products independent of their properties and saturation levels. Here, it is believed to be beneficial to use NMR measurements to investigate absorbent articles (also called "hygiene products" herein) that can consist of different layers of porous materials (e.g., diapers and catamenial devices). These absorbent articles have a specific structure designed to function in the best way possible, and therefore each layer has certain roles to fulfill. For instance, the Top-Sheet layer (TS) is generally designed to absorb fluid as fast as possible and to transport it to a core layer in order to give a better dryness feeling to the wearer. Non-woven materials can be used in different layers of an absorbent article such as the TS layer, the Secondary-Top-Sheet (STS) layer and the Core-Cover (CC) layer. These materials can be provided as thin layers. The thinness of these layers can result in current simulation efforts failing to predict internal properties and fluid handling and fluid flow dynamics (e.g., permeability and capillary pressure). Thus, one of skill in the art will appreciate that a process having the capability to measure critical properties like fluid kinetics and distribution can have high importance.

As discussed supra, it is a challenge to obtain accurate information on the internal liquid distribution of an absorbent article. In order to have a better understanding of the functionality of these materials and to compare different materials and products in the context of fluid distribution and kinetics, a series of experiments has been designed and performed that incorporates a NMR-MOUSE device. One of skill in the art will recognize that a method incorporating a portable NMR-MOUSE can be advantageous by providing an ability to provide in-situ testing. The time consuming procedure of image processing and data acquisition is a drawback of the other methods such as CT, MRI, and X-Ray whereas the data obtained from NMR-MOUSE are easy for interpretation. A fast data acquisition in combination with a high resolution to follow the kinetics inside hygiene products at low cost can be achieved with this method.

Additionally, the total running time of an absorbent article test can be an important driving factor. Therefore, it can be desirable to have a relatively short experiment time. To this end, the use of a contrast agent that decreases the $T_1$ relaxation time of protons within the absorbent article independent of the material type and its saturation level for profiling the fluid distribution within an absorbent article can reduce the time necessary to execute the process. In any regard, the contrast agent should preferably not affect the absorbent article, the materials that form the absorbent article, and/or the behavior of the fluid insulting the absorbent article.

Figure 3:
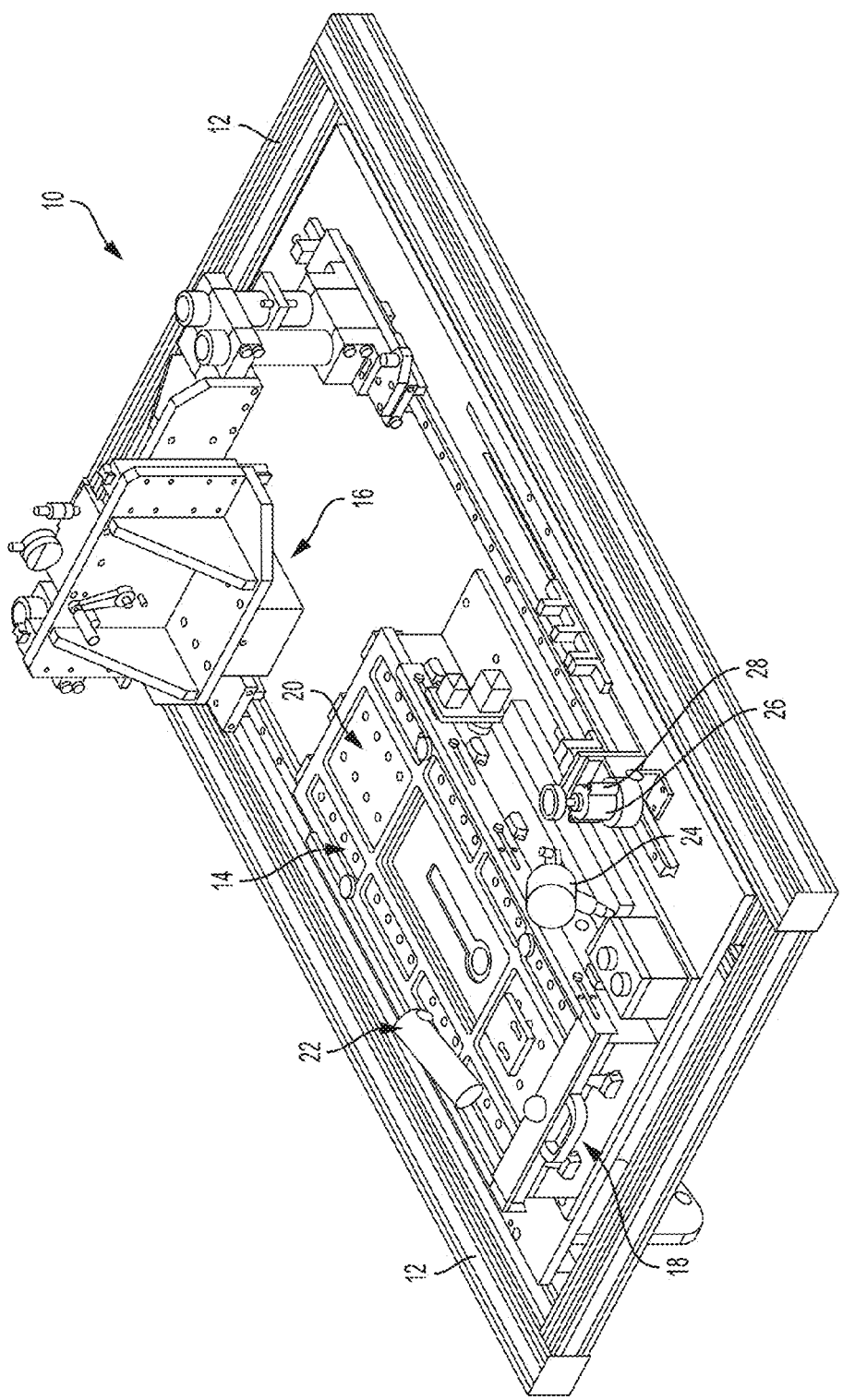
FIG. 3 is a perspective view of an exemplary device for measuring fluid distribution in absorbent articles in two and three dimensions consistent with the present disclosure.
Figure 4:
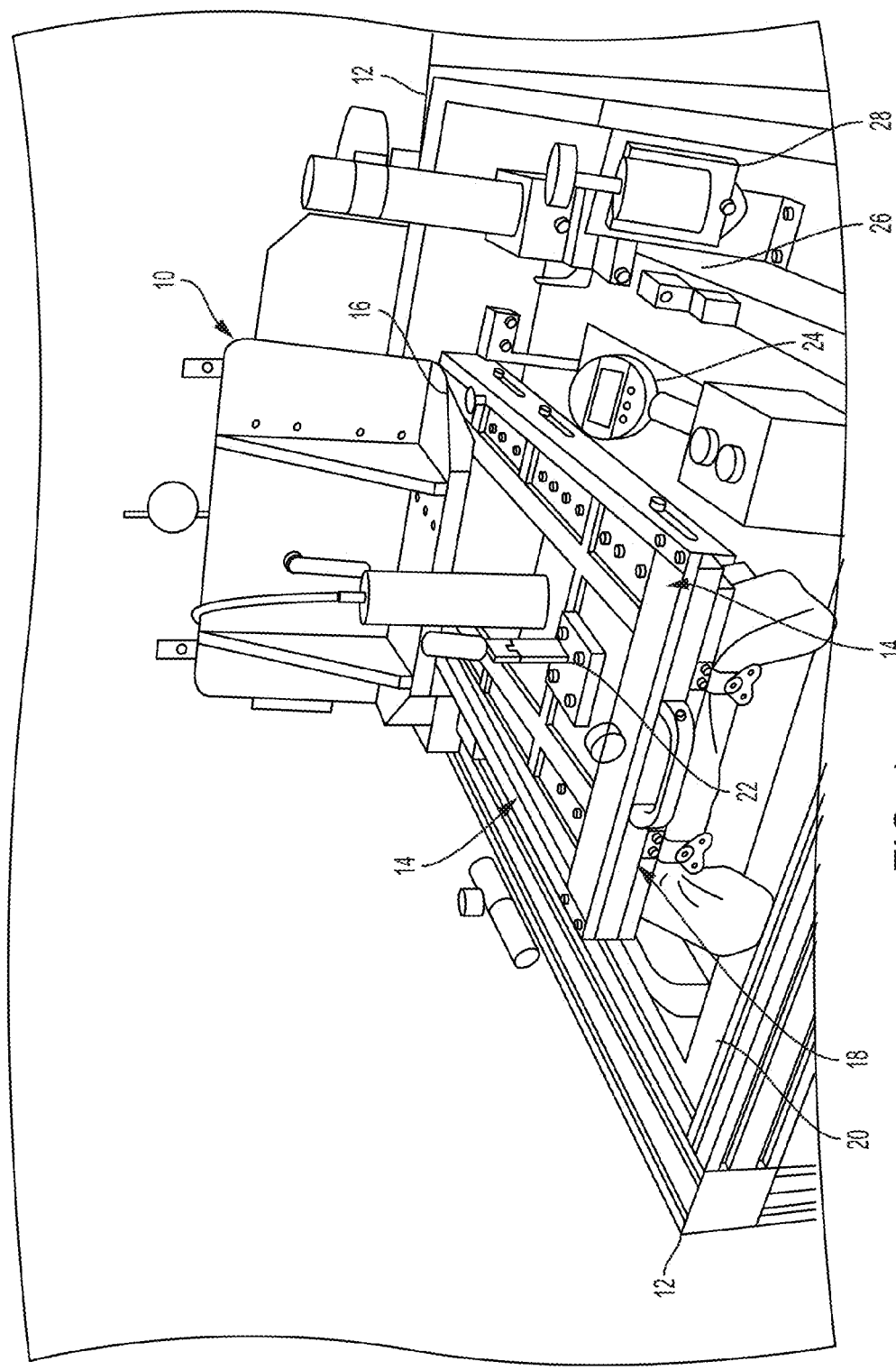
FIG. 4 is a photograph of an alternative perspective view of the exemplary device for measuring fluid distribution in absorbent articles in two and three dimensions of FIG. 3.

A device suitable for a process to provide a better two- and three-dimensional profile of the fluid distribution through a multi-layer absorbent article such as a diaper or a catamenial device is shown in FIGS. 3-4. The device 10 is generally comprises a frame 12, a pressure chamber 14, and an NMR sensor 16. The pressure chamber 14 is generally formed from a conformable and pressurizable surface such as exemplary bladder assembly 18 and a top plate assembly 20 which includes a deposition assembly 22. It is believed that a conformable and pressureable surface can provide a benefit in the application of a uniform pressure across a contoured surface, which is maintained even as the absorbent article is swelling non-uniformly during fluid acquisition and redistribution. Additionally, it is believed that a conformable and pressureable surface can provide the ability to study fluid acquisition and redistribution under different amounts of pressure.

As used herein, the term "bladder assembly 18" is intended to include all forms of conformable surfaces reactive to a pressure applied thereto and should be construed in its broadest form to accommodate all forms of conformable surfaces suitable for the disposition of articles disposable between the conformable surface (e.g., exemplary bladder assembly 18, an expandable foam, other pressurizeable structure and materials, and the like) and top plate assembly 20.

An exemplary, but non-limiting, bladder assembly 18 can be constructed of 12.7 mm Plexiglas to provide an overall dimension of 80 cm long by 30 cm wide by 5 cm tall. A manometer 24 can be provided for the measurement of the pressure inside the pressure chamber 14. A pressure gauge 26 can be provided to regulate the introduction of air into the pressure chamber 14 and can be positionably installed through access holes cooperatively disposed upon the right side of pressure chamber 14. One of skill in the art will understand that the manometer 24, a pressure gauge, and the pressure regulator 28 can be positioned anywhere upon pressure chamber 14 that provides efficacious positioning of the equipment as well as the ability to measure and/or adjust the pressures disposed within pressure chamber 14 as required by the end user.

Figure 5:
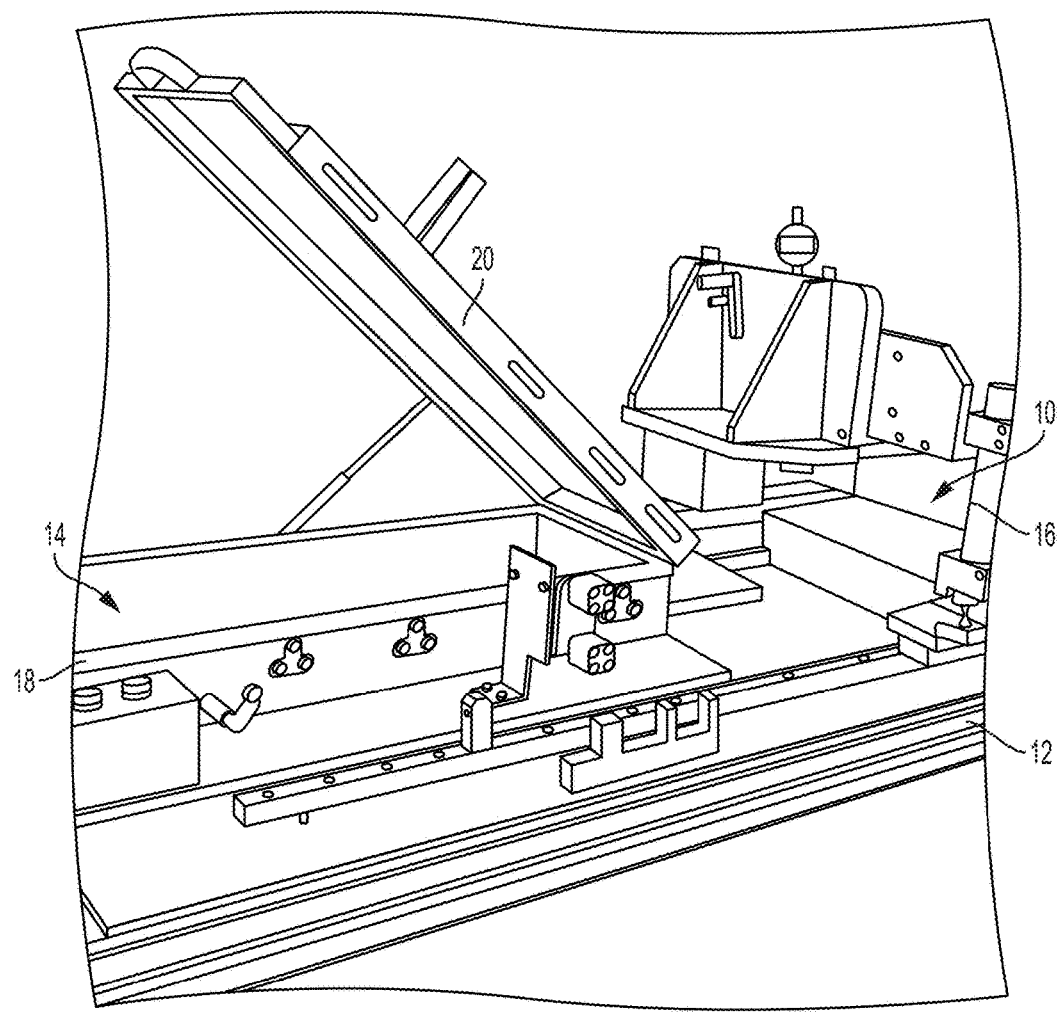
FIG. 5 is a photograph of an alternative perspective view of the exemplary device for measuring fluid distribution in absorbent articles in two and three dimensions of FIG. 3 where the top plate and bladder assembly of the pressure chamber are separated for sample insertion.

FIG. 5 provides an exemplary view of the device 10 showing the separable and displaceable nature of the top plate assembly 20 relative to the bladder assembly 18 of pressure chamber 14 as well as frame 12. As shown in the exemplary embodiment, the top plate assembly 20 can be attached to bladder assembly 18 and rotated about a longitudinal axis of attachment of top plate assembly 20 to the bladder assembly 18 at an angle, γ, to facilitate user access to that region of the internal portion of pressure chamber 14 disposed between top plate assembly 20 and bladder assembly 18. Alternatively, and as would be understood by one of skill in the art, top plate assembly 20 can be removeably attached to bladder assembly 18. This embodiment could facilitate the complete removal of top plate assembly 20 from bladder assembly 18 to allow a user access to the entire internal portion of pressure chamber 14 disposed between top plate assembly 20 and bladder assembly 18. A compression, hydraulic, pneumatic, or mechanical cylinder or other mechanism 30 can be used by one of skill in the art to secure top plate assembly 20 relative to bladder assembly 18 at a desired angle, γ, that facilitates user access to the internal portion of pressure chamber 14 disposed between top plate assembly 20 and bladder assembly 18.

Figure 6:
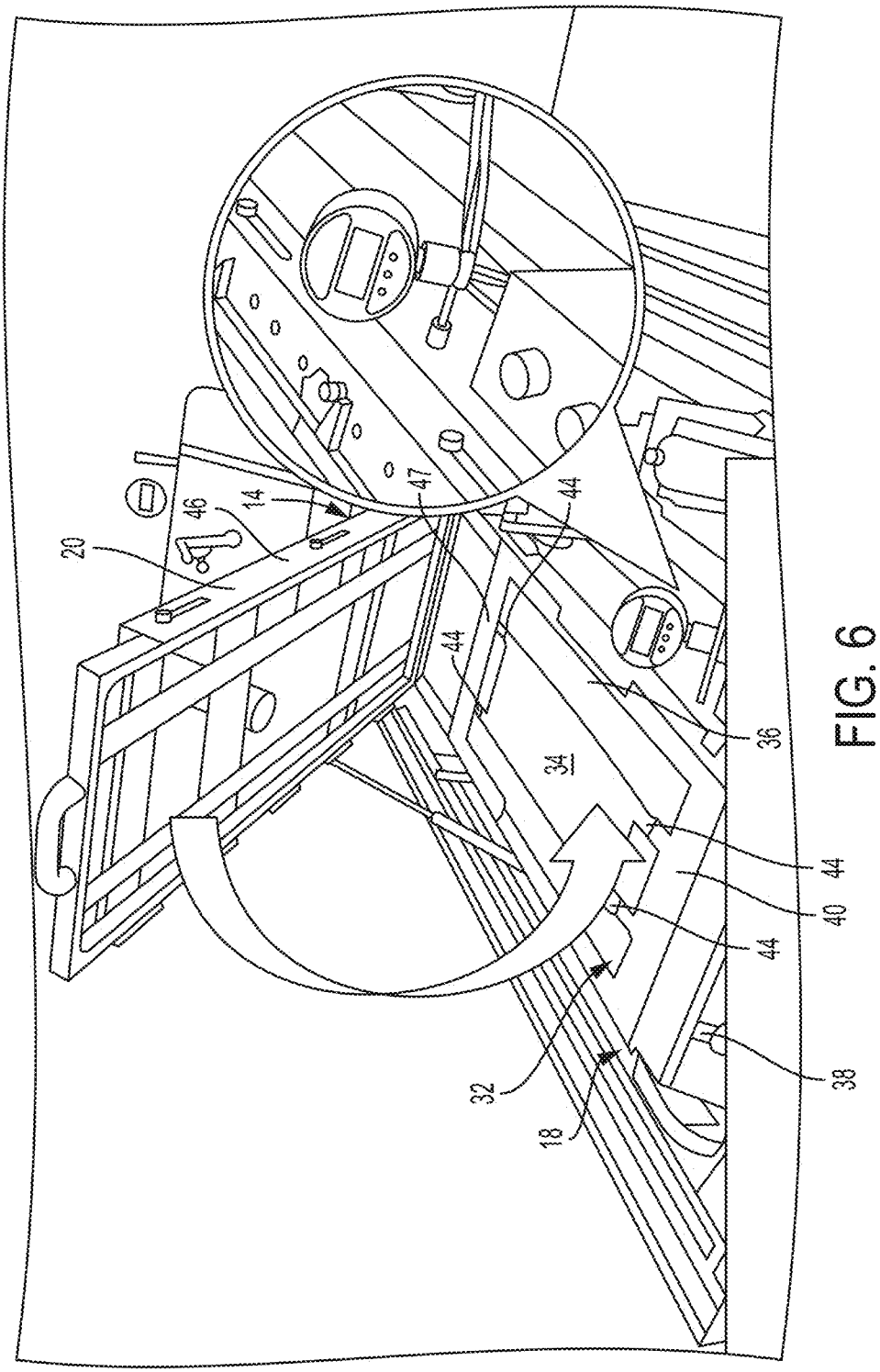
FIG. 6 is a photograph of yet another alternative perspective view of the exemplary device for measuring fluid distribution in absorbent articles in two and three dimensions of FIG. 3 where the top plate and bladder assembly of the pressure chamber are separated and a bladder and sample are inserted therein.

As shown in FIG. 6, the bladder assembly 18 of pressure chamber 14 can be provided with a bladder 32. Bladder 32 can be cooperatively associated and sealingly engaged to bladder assembly 18 of pressure chamber 14 by draping the bladder 32 over the top of bladder assembly 18 with sufficient slack to provide that the bladder 32 touches the bottom of bladder assembly 18 at its center point. An exemplary, but non-limiting, bladder 32 can be provided as a 50 mm×100 mm piece of silicone film having a thickness of 0.02 inches and a Shore A durometer value of 20. An exemplary material suitable for use as bladder 32 is available as Part#86435K85 from McMaster-Carr, Cleveland, Ohio.

Preferably, a secondary frame 36, having a fitting flange is fitted over the top of the bladder 32 and secured to the bladder assembly 18 with clamps 38. When bladder 32 is sealably secured to bladder assembly 32, it is preferred that the bladder 32/bladder assembly 32 combination assembly be leak free at a pressure of 30 psi.

A front sample support 40 and back sample support 42 can be used to anchor a sample 34 or article to be measured by the device 10 relative to bladder assembly 18. As required, the sample 34 or article can attach to the front 40 and back 42 sample supports by attachment means 44. Such attachment can be provided by an end user as would be determined by one of skill in the art.

Exemplary, but non-limiting, attachment means 44 can be provided as an adhesive tape fastening system, mechanical "hook" fasteners, adhesive attachment systems, combinations thereof, and the like. Front sample support 40 and back sample support 42 can be adjusted as may be required along the length (i.e., y-axis) of the secondary frame 36. The adjustment of front sample support 40 and back sample support relative to secondary frame 36 can be provided as a pin and hole system and the like as would be understood by one of skill in the art for the accommodation of differently sized absorbent articles to correctly align the loading point of the absorbent article.

The top plate assembly 20 can be provided by an appropriately sized Plexiglas® piece reinforced with a support frame 46 to enhance rigidity. It is preferred that the portion of top plate assembly 20 disposed proximate to the sample 34 that is disposed upon bladder 32 and proximate to the area that NMR sensor 16 will operate be essentially transparent to LF NMR radiation.

Figure 7:
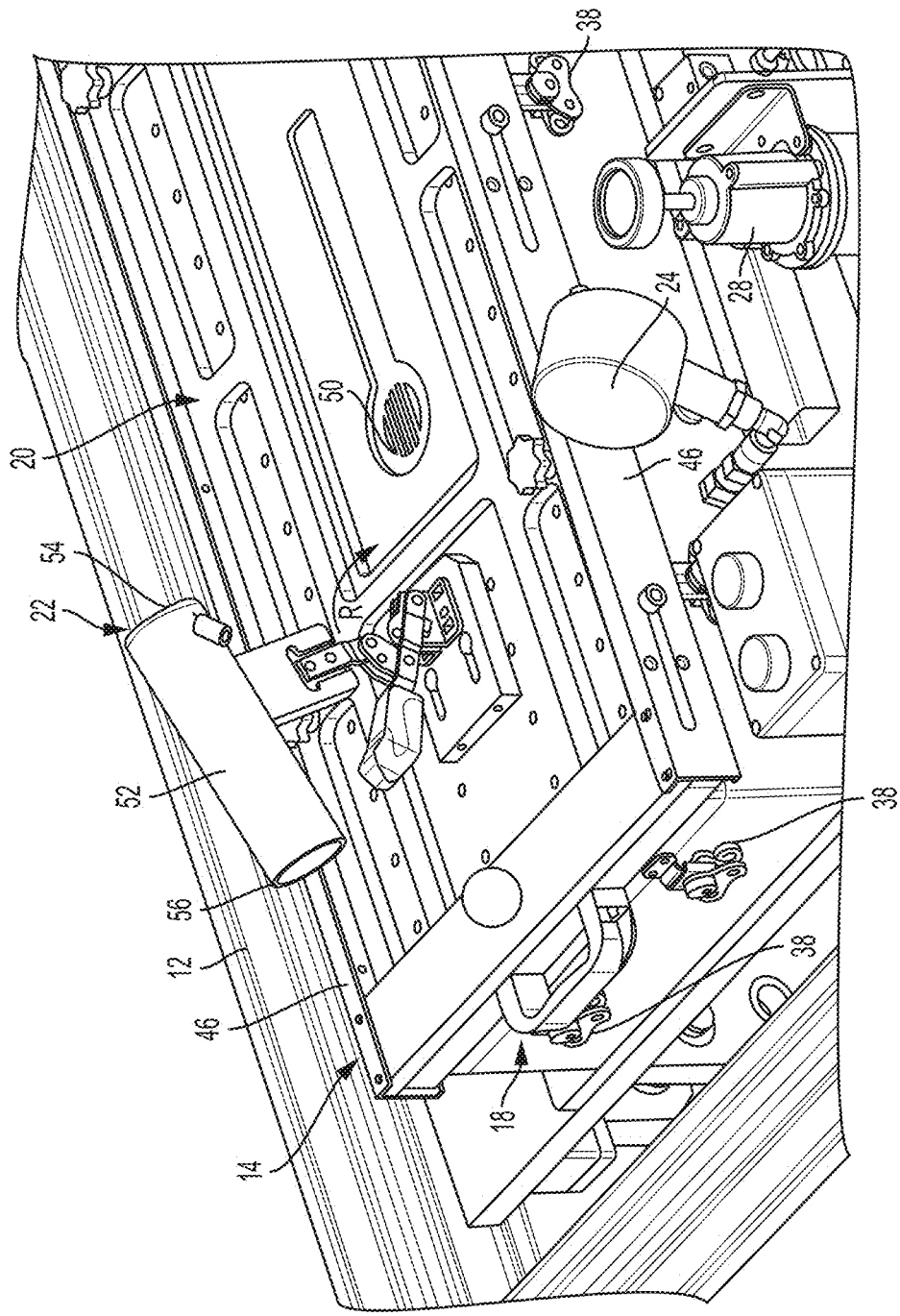
FIG. 7 is a perspective view of an exemplary deposition assembly suitable for cooperative engagement with the top plate of an exemplary pressure chamber.
Figure 8:
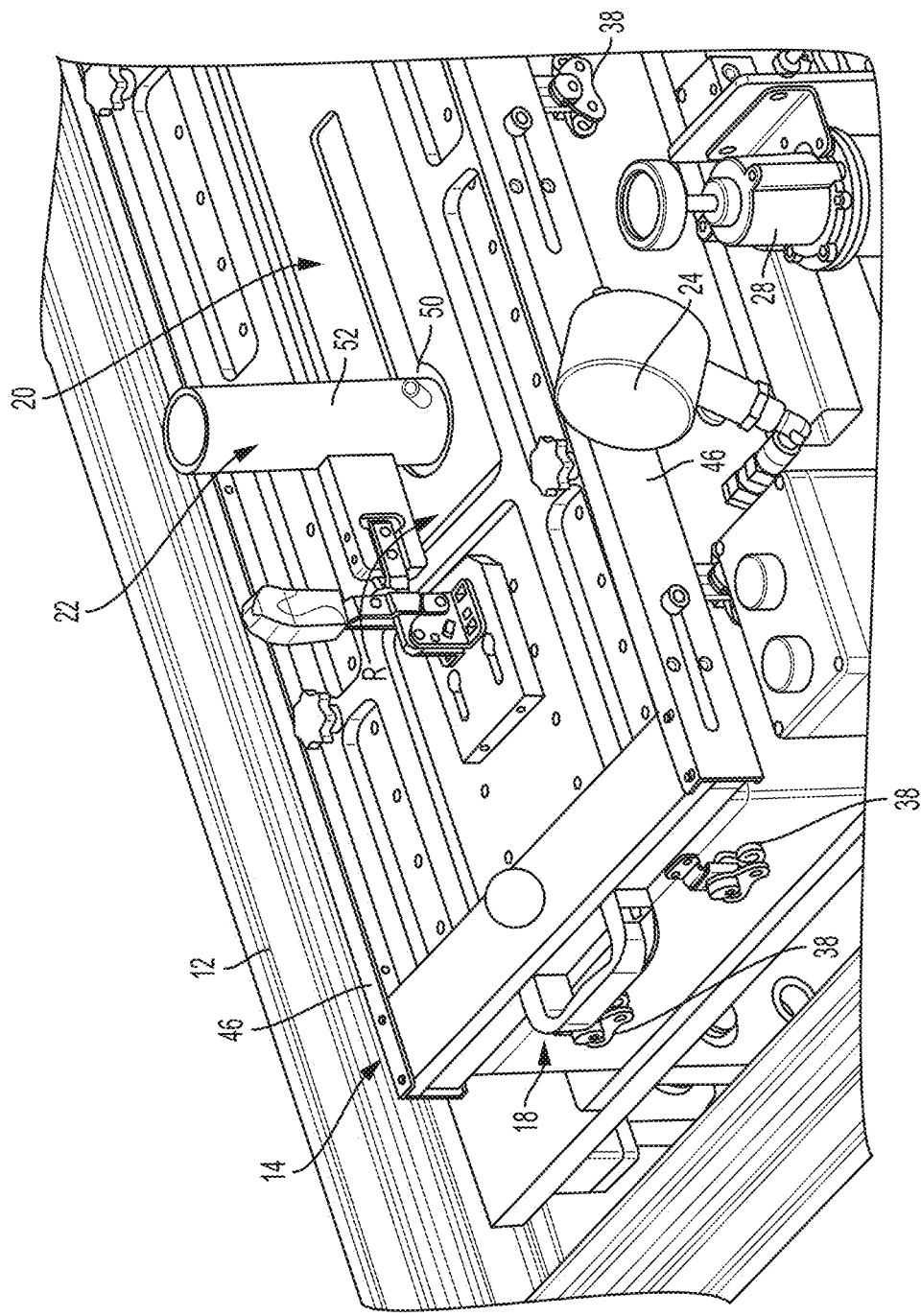
FIG. 8 is a perspective view of an exemplary deposition assembly in cooperative engagement with the insult application aperture disposed within the top plate of an exemplary pressure chamber.

As shown in FIGS. 7-8, an exemplary, but non-limiting, deposition assembly 48 can be disposed upon a surface of top plate assembly 20. Deposition assembly 22 can facilitate the deposition of an insult upon sample 34 disposed upon bladder 32 disposed within pressure chamber 14. Deposition assembly 22 is preferably rotatable about an axis, R, to facilitate the placement and displacement of deposition assembly into, and out of, contacting engagement with insult application aperture 50 disposed within top plate assembly 20. In a preferred embodiment, deposition assembly 22 is disposed so as to be located centrally relative to top plate assembly 20 and cooperatively aligned with insult application aperture 50.

One of skill in the art will appreciate that a suitable deposition assembly 22 can be constructed from a material that is transparent to NMR-level RF. An exemplary, but non-limiting material suitable for forming deposition assembly 22 can be constructed as a Plexiglas cylinder 52. When deposition assembly 22 is cooperatively aligned with insult application aperture 50, it is preferred that deposition assembly 22 be inserted through the top plate assembly 20, through insult application aperture 50 so that the contacting edge 54 of deposition assembly 22 is cooperatively aligned with the surface of top plate assembly 20 that is in contacting engagement with sample 34 disposed within pressure chamber 14. A screen or mesh (e.g., a nylon screen, scrim material, and/or a perforated glass plate) can be affixed to contacting edge 54 of deposition assembly 22 to prevent the sample 34 from swelling into the cylinder 52. If desired, a cap (not shown) can be fitted upon non-contacting edge 56 cylinder 52 forming deposition assembly 22. A cap so applied to the non-contacting edge 56 cylinder 52 forming deposition assembly 22 can be provided with an aperture (not shown) to ensure that any negative pressure disposed within cylinder 52 forming deposition assembly 22 does not impede the absorption speed of an insult disposed upon sample 34.

One of skill in the art would be able to provide pressure-reducing apertures within top plate assembly 20. Such apertures can prevent air from being trapped under top plate assembly 20 as the bladder 32 is inflated but not to allow an insult applied to sample 34 through insult application aperture 50 to escape. One of skill in the art will appreciate that the device 10 is formed by the unique combination of a LF NMR sensor 16 in conjunction with the pressure chamber 14. An exemplary NMR sensor 16 can be provided as a single-sided NMR capable of producing depth profiles with microscopic spatial resolution. It would be recognized by one of skill in the art that an exemplary NMR sensor 16 can be provided with an open geometry that can provide a non-invasive and non-destructive testing method to characterize the depth structure of objects of arbitrary size. Such an exemplary NMR sensor 16 can provide a permanent magnet geometry that generates one plane of constant magnetic field intensity parallel to the scanner surface. A thin flat sensitive slice can be defined by combining the highly uniform static gradient with selective RF excitation. By moving the relative position between the slice and the object, one-dimensional profiles of the near surface of large samples can be produced with high spatial resolution.

An exemplary NMR sensor 16 can be provided with neodymium-iron-boron (NeFeB) magnets and an iron (Fe) yoke. An exemplary NMR sensor 16 can provide a magnetic field having a quadratic field behavior at the surface that becomes flat at a distance that depends on the gap, Gs, chosen between the magnets of NMR sensor 16. For example, the magnetic field at a distance of 15 mm from the surface and in the center of the NMR sensor 16 can be provided with a strong uniform gradient along the about the longitudinal axis of the array of magnets. This can define a plane of constant field intensity parallel to the surface with a field variation smaller than 0.1 mT along the longitudinal axis. This can be achieved by choosing a RF coil having suitable dimensions.

The RF coil and tuning circuit used in combination with the magnet should generally satisfy a number of needs. First, the dimension of the coil can be determined by the lateral dimensions of the sensitive region where the magnet system defines a flat slice. Second, the coil should have a low inductance in order to reduce any detuning generated during the scanning procedure. This can involve movement of the sensor with respect to the sample to be analyzed and can change the load of the coil. Third, the maximum depth desired can determine the distance at which the coil should be positioned away from the magnet surface.

A preferred RF coil used to fulfill these requirements can be provided as a two-turn rectangular coil wound with copper wire. A parallel tank-circuit can be used for tuning and matching of the RF coil. An exemplary 10.6 MHz L-C tank circuit suitable for tuning the RF coil can be assembled with a low inductance of about 0.12 pH and 2000 pF. This L-C tank circuit can provide a nominal circuit quality factor, Q, of 65 which leads to a dead time of about 25 μsec. By introducing a resistance in parallel to the coil, the Q of the L-C tank circuit can be reduced to lower the dead time. For example, a coil having an overall resistance of 270Ω can reduce the L-C tank circuit Q to 18 providing an exemplary dead time of about 7 μsec.

An exemplary NMR sensor 16 can also incorporate a system to adjust the position of the magnet forming the magnet array of NMR sensor 16 relative to a sample disposed thereupon. For example, a mechanical lift device can position the magnet array of NMR sensor 16 at a desired distance relative to the sample 34. The position of the magnets associated with the NMR sensor 16 can be controlled by a high-precision screw controlled by a stepper-motor as would be recognized by one of skill in the art.

Accordingly, the NMR sensor 16 is preferably arranged to generate a sufficiently homogeneous magnetic field over a volume, $V_a$, located at a location along the z-axis in the sample 34 thereby causing excitation of subject nuclei in the volume $V_a$, and to detect radio frequency emissions from the subject nuclei in the volume $V_a$ by using an optimized CPMG pulse sequence in combination with the use of contrast agent. The apparatus is preferably arranged to, substantially immediately following excitation of volume $V_a$, cause excitation of subject nuclei in a volume, $V_b$, where $V_b$ is a volume differing from $V_a$ only in its position along the longitudinal axis, and to detect radio frequency emissions from the subject nuclei in the volume $V_b$.

To enable the quantification of liquids in a sample 34 (such as absorbent hygiene materials and products), an optimized CPMG pulse sequence in combination with a contrast agent can make the $T_1$ and $T_2$ times independent of the sample 34 (and the parts thereof) and the sample 34 saturation levels that can enable the fast quantification of liquids inside the sample 34. In a preferred embodiment, the NMR sensor 16 can be provided with an optimized CPMG pulse sequence (discussed supra) having a 90° x-pulse followed by a refocusing pulse of 180° y-pulse (i.e. $T_2$ has to be long enough and echo time the short to avoid $T_2$ weighing of the NMR signal). It is believed that $T_1$ should independent of material type and short enough to allow a repetition time inside the sequence of 200 ms enabling the quantitative measurements of fast kinetics (4-5 Hz) and fast measurement time for liquid distributions.

Such an optimized CPMG pulse sequence in combination with the use of a suitable contrast agent can allow for the collection of NMR Amplitude data (in arbitrary units, a.u.) versus depth (in m) as the high precision lift of NMR sensor 16 sequentially steps through the sample 34 depth and to measure the kinetics of a fluid disposed within a defined volume disposed inside the sample 34.

To enable the quantification of liquids using below mentioned parameters the $T_1$ relaxation time should be below 50 ms and a $T_2$ above 20 ms, independent of material type and its saturation level. An exemplary NMR sensor having a gradient of 8 T/m, a measuring frequency of 13.5 MHz, and a quadratic surface coil with dimension of 40 mm can be used to excite a sensitive slice with a certain thickness, which is proportional to the bandwidth of the RF-pulse according to the following equation:

$$\Delta z = 2\pi \Delta v / G_z \gamma$$

Where, $\Delta v$ is bandwidth, $G_z$ is gradient and $\gamma$ is the gyromagnetic ratio. In the CPMG sequence, the thickness of the sensitive slice could be adjusted with number of acquisition points (m) in each echo and dwell time (dw) where the acquisition window s:

$$m \cdot dw$$

Furthermore, the thickness of the sensitive slice can be the same as measuring step size. Exemplary, but non-limiting values for a suitable CPMG pulse can provide for a liquid adjusted to a $T_1 < 50$ ms and a $T_2 > 20$ ms suitable for kinetic and profiling analysis:

Repetition Time for kinetic analysis=200 ms
Repetition Time for profiling analysis=500 ms
90° Amplitude=−7 dB
180° Amplitude=0 dB
Pulse Length=5 μs
Echo Time=90 μs
Number of Echoes for kinetics=128
Number of Echoes for profiling=8
Echo Shift=1 s
Rx Gain=31 dB
Number of Scans for kinetics=1
Number of Scans for profiling=8

By way of non-limiting example, $T_2$ can be greater than 20 ms, Echo Time <100 μsec, Number of Echoes <128 for kinetics and Number of Echoes <32 for profiling. $T_1$ can be set to 5 $T_1$. It may be advantageous to use a contrast agent that enables a constant $T_1$ independent of material type and its saturation level and a fast repetition time (scanning rate) of 5 $T_1$.

The longitudinal relaxation time ($T_1$) of a contrast agent solution in different saturated hygiene materials can be measured by means of a standard-inversion recovery method. The type of contrast agent and its concentration can be calculated by applying the following equation:

$$(1/T_1)\text{obs} = (1/T_1)d + r_1 \cdot C$$

Where:
C=concentration of e.g. the gadolinium ion,
(1/T) obs=observed relaxation rate,
(1/T) d=relaxation rate of water protons,
[$r_1$] relaxivity is a specific parameter for each contrast agent that could be measured.

This can be used to find a suitable contrast agent.

Rx Phase can be determined during the phase adjustment. It was surprisingly found that a value of 230° was acceptable. It was also surprisingly found that pulse length can depend on measurement depth which can be adjusted as required.

In order to translate signal output into quantitative information on detected liquid volume, the NMR sensor 16 can be calibrated. NMR sensor 16 calibration is done with the use of liquid mixture of the experimental wetting solution and deuterium oxide ($D_2O$), where the latter serves as a solvent giving no NMR signal. The procedure starts from preparation of mixtures of different component ratios. The ratio range should be broad enough to cover expected limit of detection, maximum wetting solution content and values in between. When testing requires contrast agent to be present in the fluid, it is preferred that each of the calibration solutions should also contain the appropriate concentration of contrast agent. Adding contrast agent to only one solution would lead to dilution of its concentration when mixing both liquids afterwards.

In a non-limiting example, NMR sensor 16 calibration is done with 0.9% saline and $D_2O$, both with addition of 2 mM/L Diethylenetriaminepentaacetic acid gadolinium (III) dihydrogen salt (available from Sigma Aldrich). The calibration range covers saline content of 0, 0.5, 2.5, 5, 10, 20, 40, 80, and 100%. Different ratio mixtures are prepared twelve (12) hours prior testing as to ensure proper mixing of the components. Calibration samples are conditioned and all testing is performed at 23° C.±1° C. The mixtures are then placed into top-covered rectangular cuvettes, preventing accumulation of air bubbles inside. In order to preclude sample positioning inconveniences, the dimensions of the cuvette should be larger than the sensitive area (4 cm×4 cm) of the NMR sensor 16 and volume (4 cm×4 cm×0.02 cm) of the determined NMR slice. The cuvettes are placed under the sensor one by one and measured using the profiling and kinetics tests. For better convenience, profiling is advised to be performed first and it should cover the whole depth of the cuvette. Profiling parameters can be set as follows:

Repetition Time=500 ms
Number of Scans=8
Number of Echoes=8
Resolution=50 μm
Step Size=–50 μm Knowing the center position within the cuvette due to profiling, NMR sensor 16 is then placed in this certain spot as to acquire kinetics signal from the middle portion of the liquid volume. Kinetics parameters set as below:

90° Amplitude=–7 dB
180° Amplitude=0 dB
Repetition Time=200 ms
Echo Time=90 μs
Number of Echoes=128
Number of Scans=1

The raw calibration data for profiling and kinetics needs to be correlated with the actual volume of 0.9% saline excited by the NMR sensor 16 with a gradient of 8 T/m at 13 MHz. In the assumed case, the profiling depth reaches 1.5 mm, while the area of the sensor covers 3.61 $cm^2$ (sensor 1.9×1.9 cm). The total volume covered by the profiling results then in 541.5 μL. On the other hand, NMR sensitive volume for kinetics is set to 200 am, resulting in 72.2 μL for the NMR slice in kinetics. Knowing the entire volumes for both modes, saline volumes may be easily recalculated taking into consideration 0.9% $NaCl:D_2O$ ratio in the particular mixtures. If the miscibility of $D_2O$ and a desired test solution does not match, perform a one point calibration (100% solution without $D_2O$). In depth studies on different saturated porous media showed a high linearity $r^2 > 0.99$ for the liquid quantification for the kinetics and profiling (e.g., for Paper Industrial Fluid (PIF) has been revealed).

While reviewing the profile data, the NMR signal can be related to the area under the curve in the signal vs. position graph. An area vs. liquid volume correlation may be obtained by integrated area for each of the examined saline content case and knowing the particular saline volumes. A calibration curve for profiling can be derived by graphically reviewing the linear trend. Limits of detection and quantification (3σ and 9σ respectively) can be established from the signal noise standard deviation for a sample containing 100% $D_2O$.

The average signal amplitude for each sample can be calculated to determine calibration curve for a kinetics profile. A linear calibration equation can then be determined from the values of the excited saline volume. Limits of detection and quantification (3σ and 9σ respectively) can be established from value of signal noise (standard deviation) for sample containing 100% $D_2O$.

Figure 9:
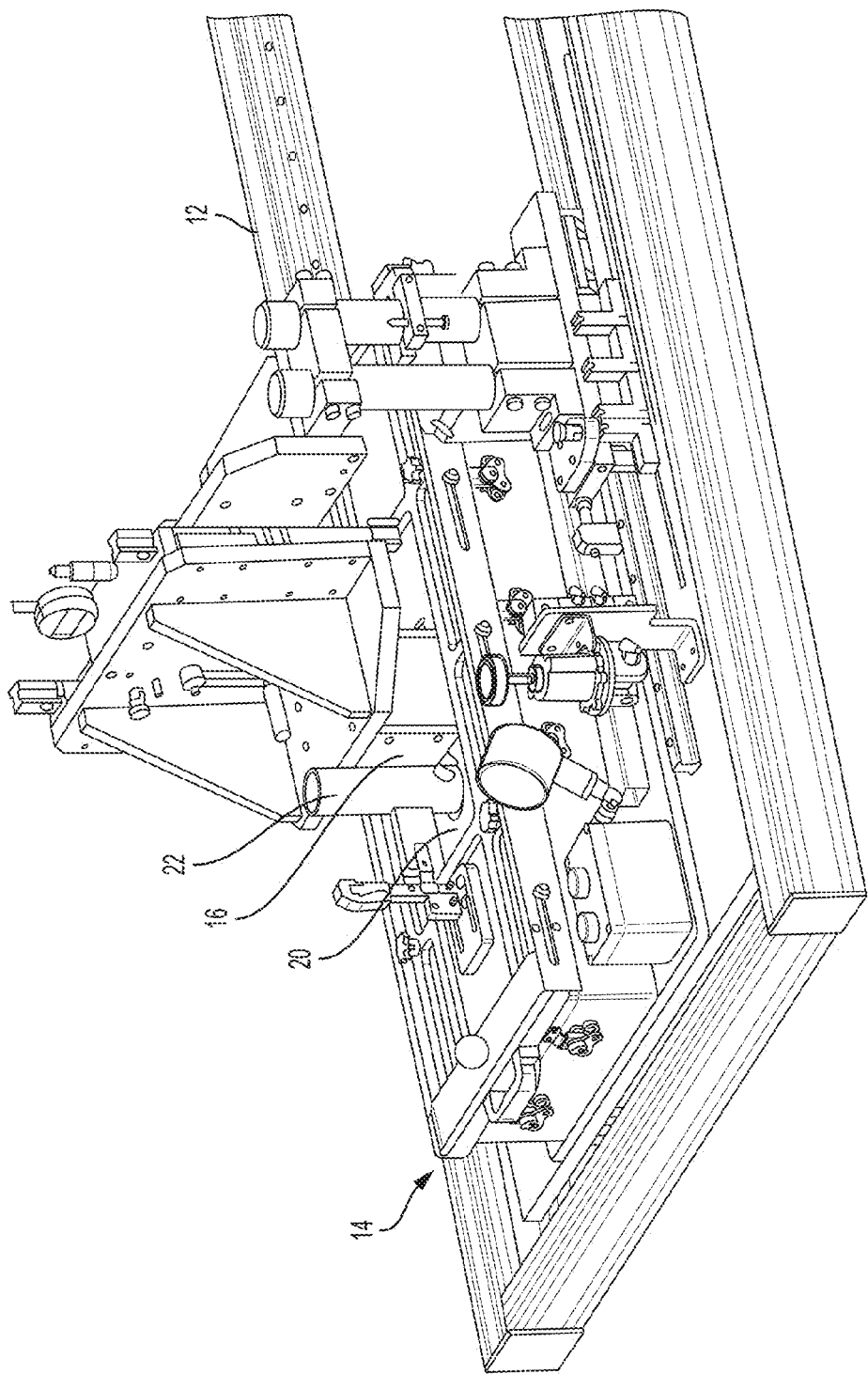
FIG. 9 is a perspective view of a device for measuring fluid distribution in absorbent articles in two and three dimensions where the NMR sensor is disposed proximate to a sample disposed within the pressure chamber.
Figure 10:
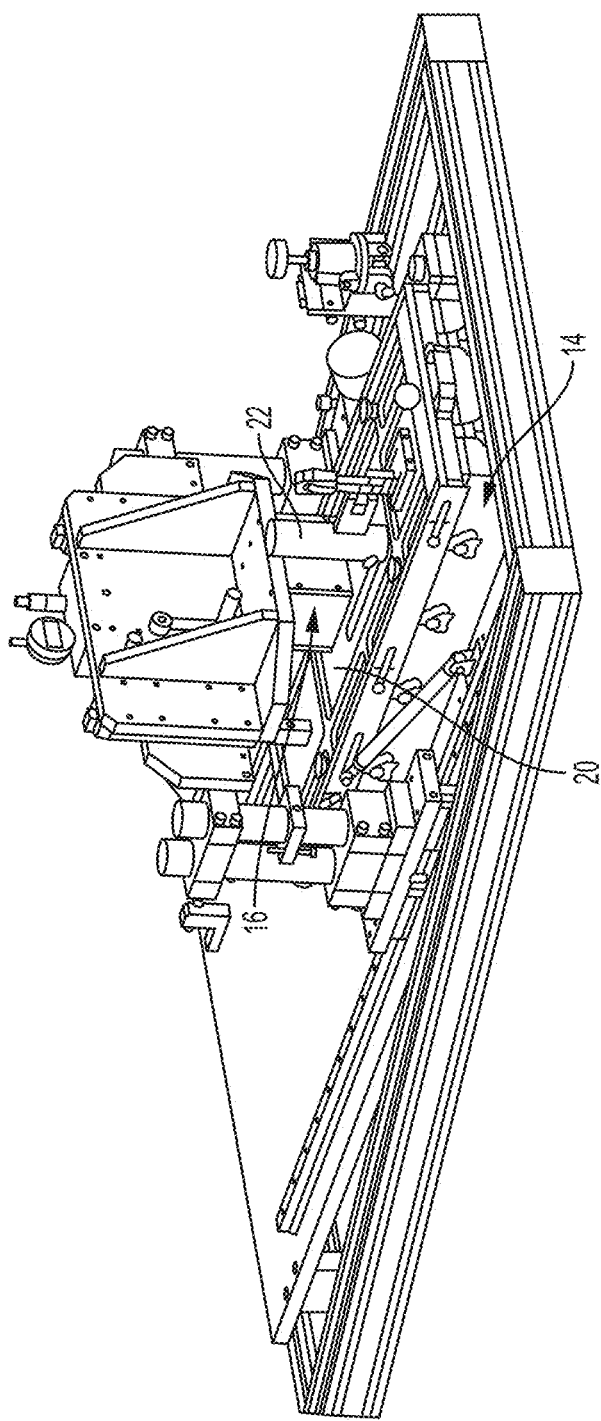
FIG. 10 is an alternative perspective view of the device for measuring fluid distribution in absorbent articles in two and three dimensions of FIG. 9 where the NMR sensor is disposed proximate to a sample disposed within the pressure chamber.
Figure 11:
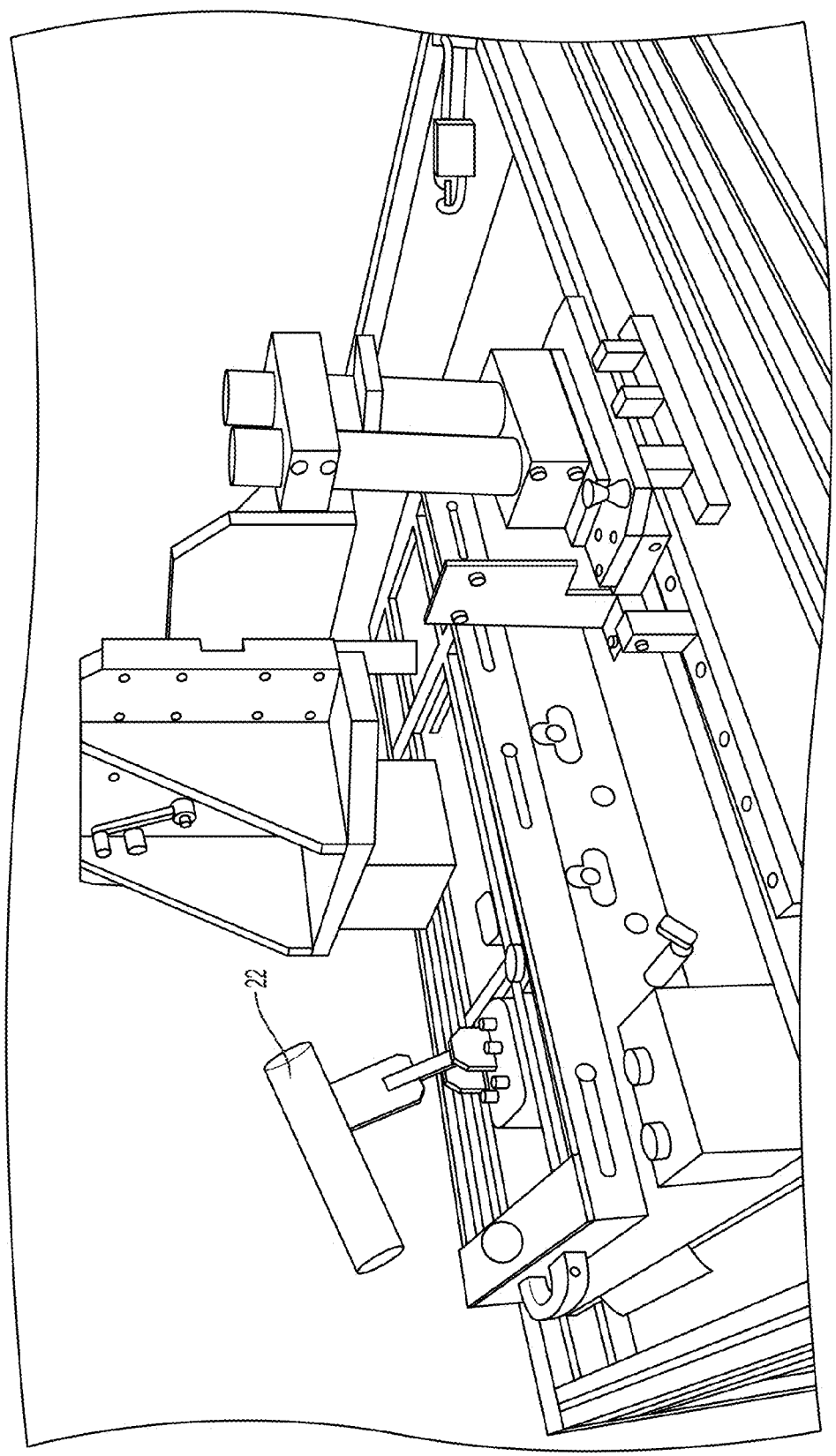
FIG. 11 is a photograph of the device for measuring fluid distribution in absorbent articles in two and three dimensions of FIG. 9 where the NMR sensor is disposed proximate to a sample disposed within the pressure chamber.

Referring to FIGS. 9-11, an exemplary NMR sensor 16 (a suitable exemplary, but non-limiting, NMR sensor 16 being described supra) is provided proximate to, and in cooperative engagement with the frame and top plate assembly 20 of pressure chamber 14. It is preferred that NMR sensor 16 be positioned in a manner so that magnetic gradient developed by NMR sensor 16 is directed toward sample 34 disposed between the top plate assembly 20 and the bladder assembly 18 of pressure chamber 14. When provided in this configuration, NMR sensor 16 can excite a portion inside the sample 34 (e.g., known in the art as a "sensitive slice") and monitor the radio frequency emissions from the subject nuclei of sample 34 disposed within the overall magnetic volume and/or within selected regions of the overall magnetic volume created by NMR sensor 16 as an insult that is applied to the top surface of sample 34 migrates into sample 34.

It is believed that device 10 can facilitate the measurement of liquid dynamics and liquid distribution quantitatively in swelling and non-swelling samples 34. One of skill in the art will understand that this is because the distance between the NMR sensor 16 and the top layer of the sample disposed within pressure chamber 14 (as discussed supra) remains constant during swelling of the sample 34 (i.e., the field-of-view, FOV, will be independent of sample 34 swelling) as absorption of the insult applied to the sample 34 occurs.

Figure 12:
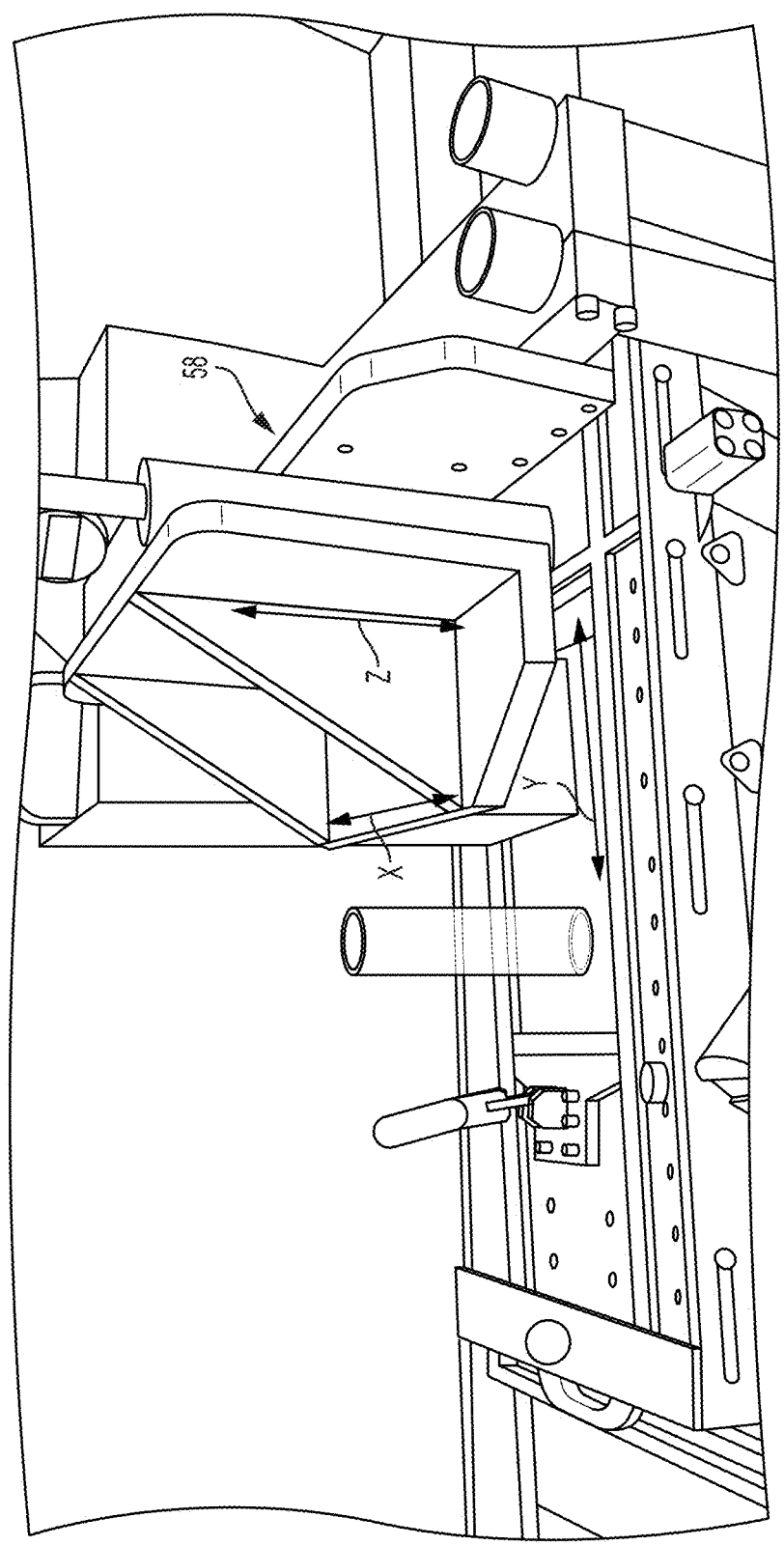
FIG. 12 is a photograph of the device for measuring fluid distribution in absorbent articles in two and three dimensions of FIG. 9 where the NMR sensor is translatable relative to a sample disposed within the pressure chamber.
Figure 13:
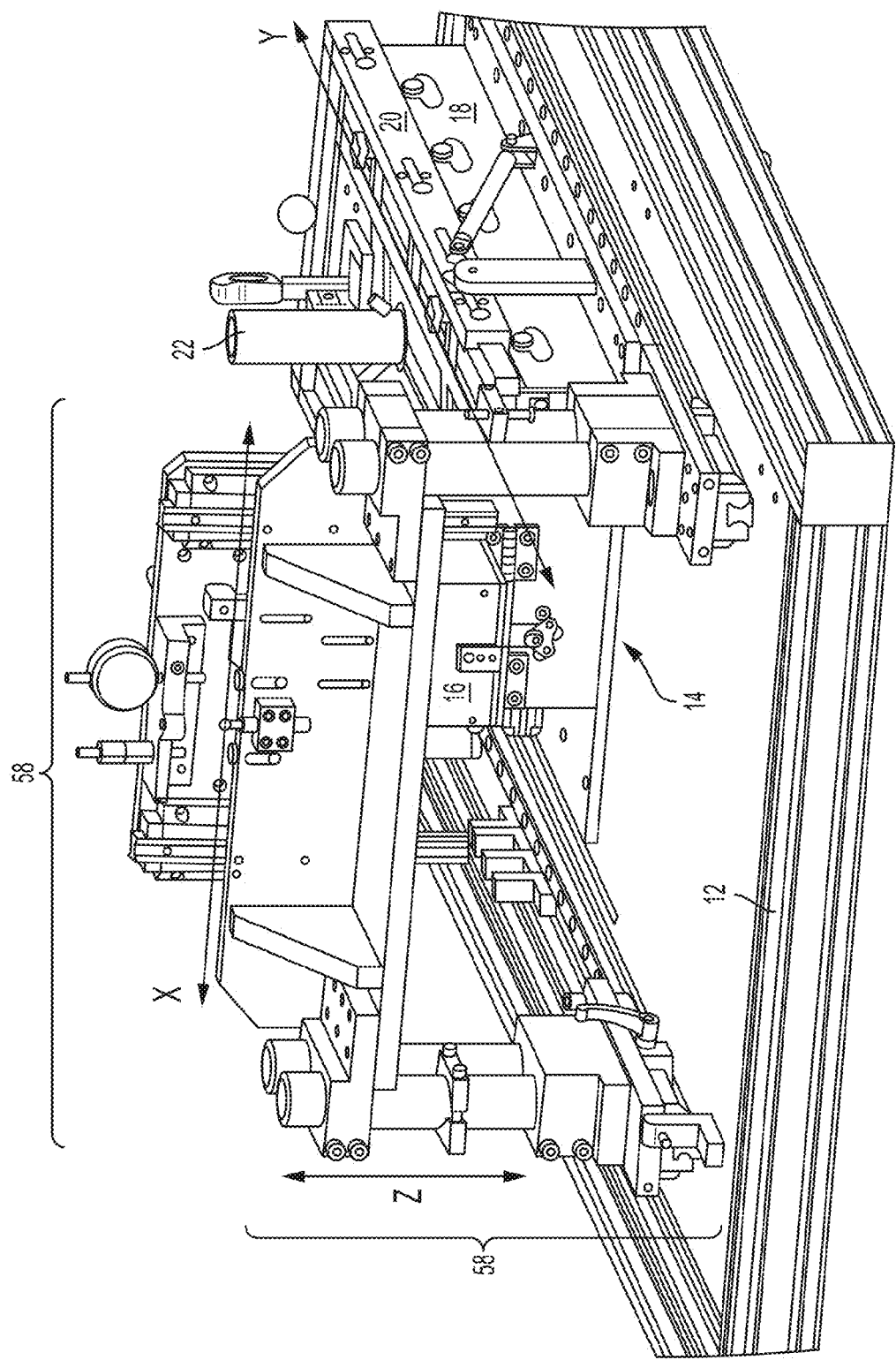
FIG. 13 is a perspective view of the device for measuring fluid distribution in absorbent articles in two and three dimensions of FIG. 9 where the NMR sensor is translatable relative to a sample disposed within the pressure chamber.

As shown in FIGS. 12-13, NMR sensor 16 can be cooperatively associated with pressure chamber 14 to provide NMR sensor 16 with at least 2- and preferably 3-axis movement (i.e., x, y, and z) relative to frame 12, pressure chamber 14, and any sample 34 disposed within pressure chamber 14. Such movement of the NMR sensor 16 can be provided to influence the constant distance of the NMR sensor 16 relative to the surface of sample 34 during the introduction of any insult thereto.

By way of non-limiting embodiment, 3-axis movement can be provided for NMR sensor 16 by a positioning plate 58 that is cooperatively attached to, and engaged with, NMR sensor 16. Positioning plate 58 can provide a desired longitudinal movement (i.e., MD or y-axis) of the NMR sensor 16 relative to pressure chamber 14 and a sample 34 disposed therein, a desired lateral movement (i.e., CD or x-axis) of the NMR sensor 16 relative to pressure chamber 14 and a sample 34 disposed therein, and/or a desired vertical movement (i.e., Z-direction or z-axis) of the NMR sensor 16 relative to pressure chamber 14 and a sample 34 disposed therein.

The ability of positioning plate 58 to manipulate the movement of the NMR sensor 16 relative to pressure chamber 14 and a sample 34 disposed therein can be provided as would be done by one of skill in the art in translational and/or positional mechanics. By way of non-limiting examples, a translational movement of NMR sensor 16 relative to pressure chamber 14 and a sample 34 disposed therein can be provided by a cam/cam follower system, mechanical actuators, hydraulic actuators, pneumatic actuators, piezoelectric actuators, electro-mechanical actuators, linear motors, telescoping linear actuator, combinations thereof, and the like. In any regard, the method of providing translational movement to NMR sensor 16 through the use of positioning plate 58 can be selected by the end user of device 10 to provide the relevant degree of accuracy in order to accomplish the measurement required by device 10.

Figure 14:
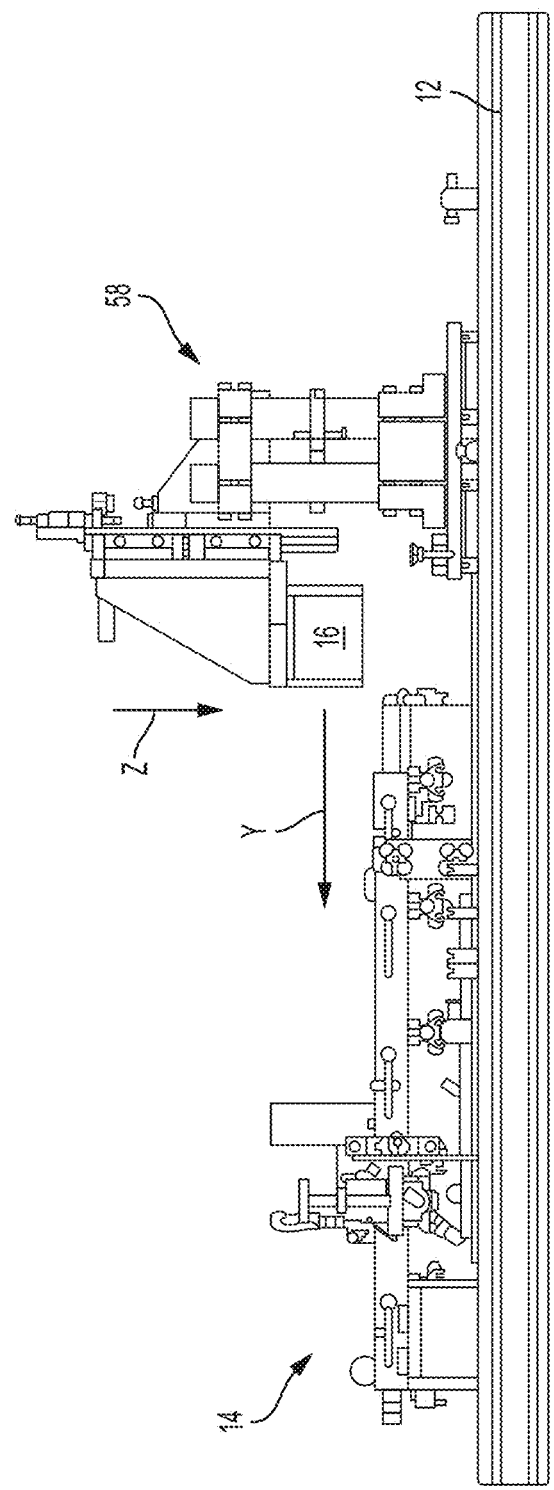
FIG. 14 is a plan view of the device for measuring fluid distribution in absorbent articles in two and three dimensions of FIG. 9 where the NMR sensor is translated away from a sample disposed within the pressure chamber.
Figure 15:
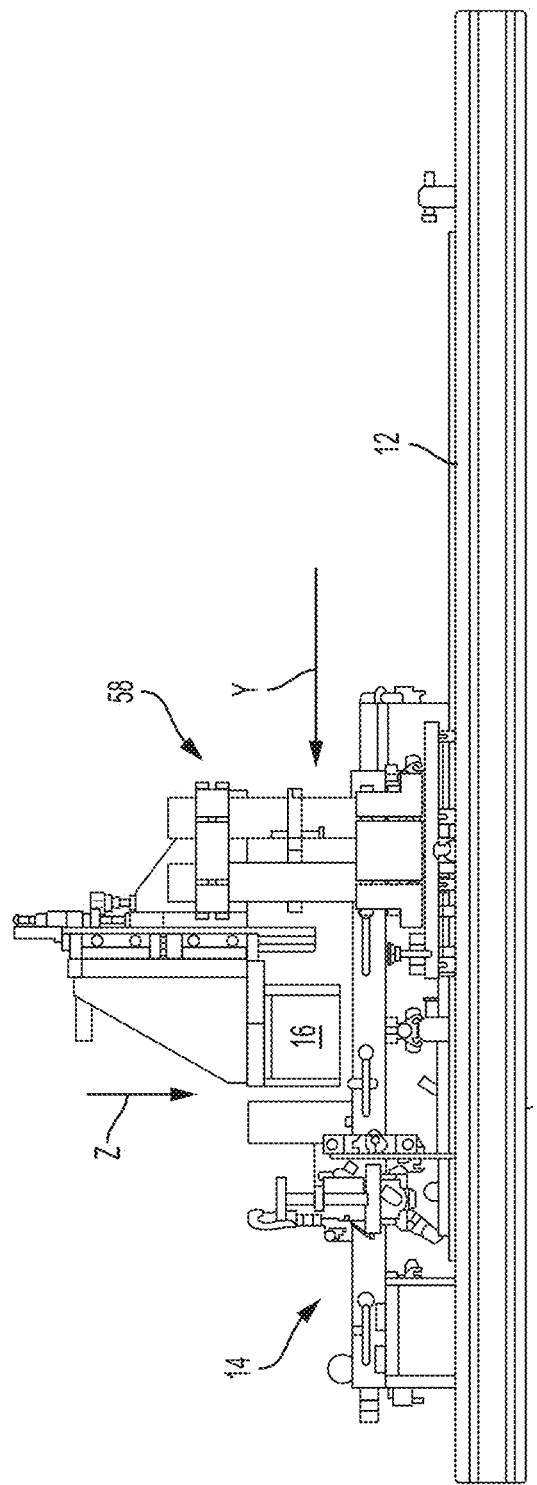
FIG. 15 is a plan view of the device for measuring fluid distribution in absorbent articles in two and three dimensions of FIG. 9 where the NMR sensor is translated proximate to a sample disposed within the pressure chamber.

Exemplary FIGS. 14-15 show the translation of NMR sensor 16 relative to frame 12, pressure chamber 14, and a sample 34 disposed within pressure chamber 14, relative to the y-axis (MD) and the z-axis (Z-direction). The advantages provided by the ability of NMR sensor 16 to translate relative to any of frame 12, pressure chamber 14, and/or sample 34 disposed within pressure chamber 14 relative to the y-axis (MD), x-axis (CD) and/or z-axis (Z-direction) would be readily recognized by one of skill in the art as providing the ability to analyze every point of sample 34 in situ. Such in situ measurements at every point of sample 34 can assist in understanding the fluid dynamics associated with the flow of a fluid within and throughout sample 34 which is instituted as an insult to the surface of sample 34 by allowing NMR sensor 34 to relocate to a desired position relative to sample 34 and observe the progress of the fluid within the sample in real-time or near real-time and provide heretofore unseen accuracy in the effort to model such fluid flow through an article 34.

Additionally, one of skill in the art will appreciate the value and advantage of providing both pressure chamber 14 and NMR sensor 16 with axial (e.g., radial) movement relative to frame 12. Without desiring to be bound by theory, it is believed that such movement of pressure chamber 14 and NMR sensor 16 relative to frame 12 can allow for the measurement of a liquid distribution in relative to any combination of the x- (CD), y- (MD), and/or z-axis (Z-direction) and as a function of the inclined product. It is believed that such 3-directional movement of the pressure chamber 14 and NMR sensor 16 relative to frame 12 can effectively simulate the flow of an insult applied to a sample 34 worn by a user.

Figure 16:
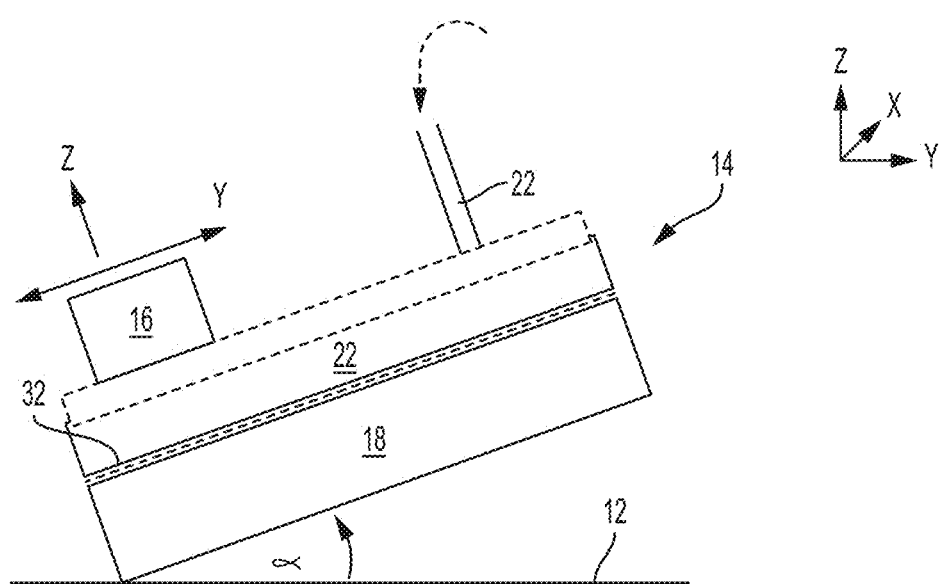
FIG. 16 is a plan view of a device for measuring fluid distribution in absorbent articles in two and three dimensions where the NMR sensor and pressure chamber are translated axially in the y-direction (MD) relative to the frame.
Figure 17:
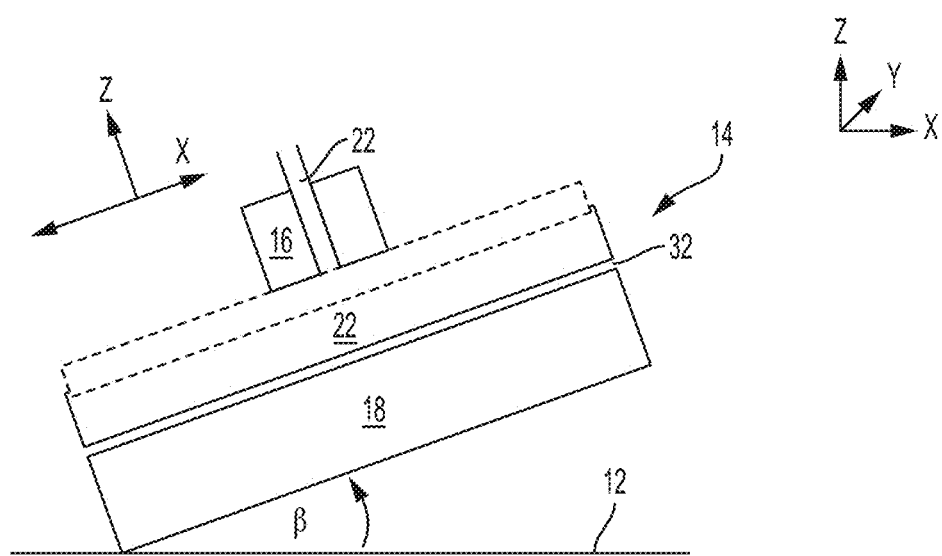
FIG. 17 is a plan view of a device for measuring fluid distribution in absorbent articles in two and three dimensions where the NMR sensor and pressure chamber are translated axially in the x-direction (CD) relative to the frame.

By way of non-limiting example, FIGS. 16-17 show the ability of the combined and cooperatively associated and engaged NMR sensor 16 and pressure chamber 14 to be rotated in any of the x- (CD), y- (MD), and/or z-axis (Z-direction) relative to frame 12. By way of non-limiting example, and as shown in FIG. 16, the combined NMR sensor 16 and pressure chamber 14 can be rotated about the x-axis relative to frame 12 through an angle, a. As shown in FIG. 17, the combined NMR sensor 16 and pressure chamber 14 can be rotated about the y-axis relative to frame 12 through an angle, β. Clearly, one of skill in the art would be able to understand and provide for the combined NMR sensor 16 and pressure chamber 14 can be rotated about both the x-axis and y-axis relative to frame 12 through a combination of angle α and angle β.

It is believed that providing the ability of the combined NMR sensor 16 and pressure chamber 14 to be rotated about any of the x-axis and y-axis relative to frame 12 can effectively provide a sample 34 disposed within pressure chamber 14 with an angle relative to the horizon that could more accurately simulate a real-life situation where the sample 34 is worn by a user and the user has assumed a reclined (or any other-than-standing) position. One of skill in the art will readily appreciate that sample 34 in the form of an absorbent article such as a diaper or a catamenial device, once applied to a human form, rarely maintains a completely flat, planar, horizontal orientation. Such an absorbent article will assume a form that conforms to the wearer and will have regions that have varying orientations relative to the horizon. Thus, one of skill in the art will appreciate the ability of the combined NMR sensor 16 and pressure chamber 14 that is adapted to be rotated relative to frame 12 can now provide the curious analyst with a more real-world analysis of fluid flow through an absorbent article by more accurately simulating, and the ability to now model, a real world wearing of the absorbent article. This ability has not been realized by any known NMR fluid flow analytical analysis and/or modeling system.

Figure 18:
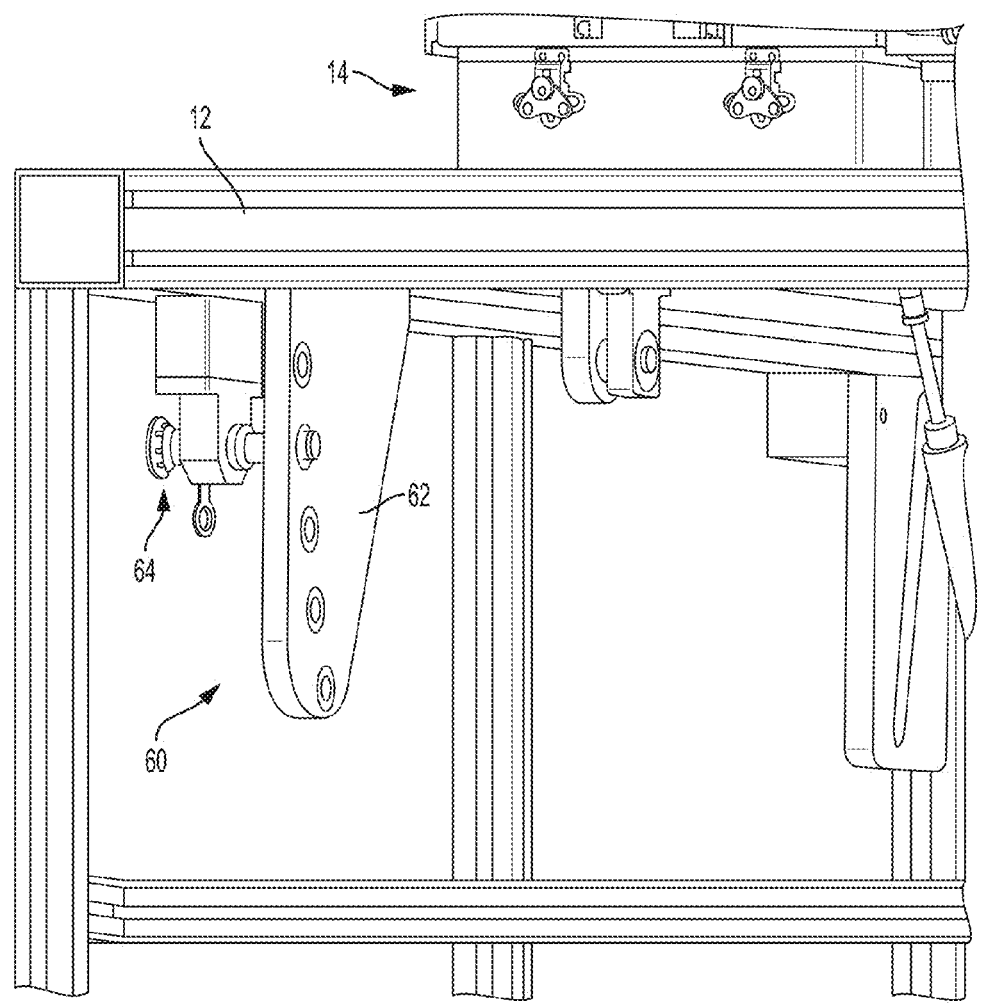
FIG. 18 is a perspective view of an exemplary rotation mechanism suitable for providing x-, y-, and z-axis rotation of the NMR sensor and pressure chamber relative to the frame.

Providing the ability of the combined NMR sensor 16 and pressure chamber 14 to be rotated about any of the x-axis and y-axis relative to frame 12 can be accomplished by any means known to those of skill in the mechanical arts. By way of non-limiting example, FIG. 18 provides for a rotation mechanism 60 having a pin 64 and hole system 62. As would be recognized by one of skill in the art, the pin 64 can be removed from a corresponding first hole disposed within hole system 62. The combined NMR sensor 16 and pressure chamber 14 can then be rotated about any of the x- and/or y-axis and the pin 64 can be engaged with a second hole disposed within hole system 62. Naturally, one of skill in the art could utilize any number of positioning systems suitable for re-orienting the combined NMR sensor 16 and pressure chamber 14 relative to frame 12. Suitable positioning systems can be provided by any suitable mechanical actuators, hydraulic actuators, pneumatic actuators, piezoelectric actuators, electro-mechanical actuators, linear motors, telescoping linear actuator, combinations thereof, and the like.

A low cost NMR test method can, for the first time, allow the end-user to quantify liquid volumes and migration inside absorbent articles at low cost. A benefit versus currently used acquisition test methods in the absorbent article manufacturing industry is that here with a low cost bench-top system, the endpoint detection of liquid absorption has been shifted from the product surface into the product which dramatically changes innovation. It allows, for the first time, a fast screening of liquid flow and distribution inside hygiene materials and products to guide development, IP, claim support and any required user-defined sample modeling.

For example, the use of device 10 can hold an absorbent article under a constant pressure from the bottom. This can allow the absorbent article to swell toward the bottom during the application of the insult to the top. Further, the device 10 can facilitate the measurement of liquid kinetics at the point where the insult is introduced to the absorbent article surface at a given or desired pressure.

The present disclosure provides a method to enable the fast quantification of liquids in a sample 34 (such as absorbent hygiene materials and products) using an optimized pulse sequence in combination with a fluid containing a suitable contrast agent, to adjust $T_1$ and $T_2$ times so that they are independent of material type and saturation level. A pulse sequence is a visual representation of the pulses and delays used in a NMR experiment. A pulse is a collection of oscillating waves with a broad range of frequencies used to rotate the bulk magnetization. Most pulse sequences have more than one pulse which can help for signal enhancement and measuring relaxation times by separation of NMR interactions.

Figure 19:
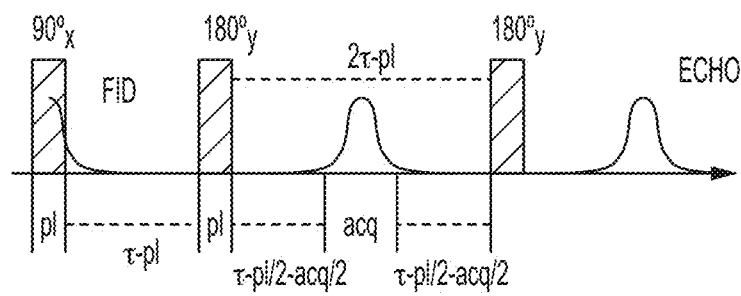
FIG. 19 is an exemplary CPMG sequence consisting of a 90° pulse followed by 180° pulses that create a train of spin echoes.
Figure 20:
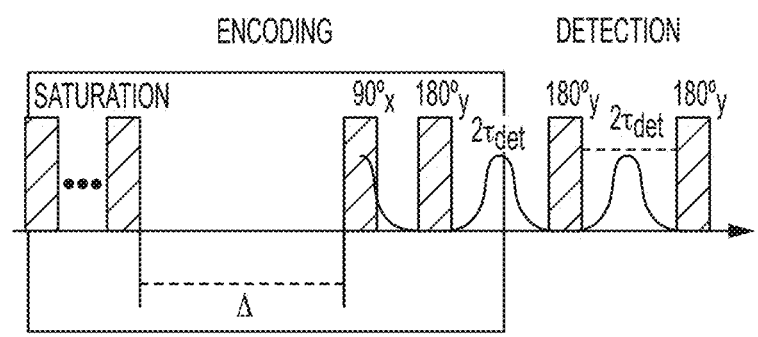
FIG. 20 is an exemplary saturation recovery CPMG sequence used to determine the longitudinal relaxation time $T_1$ having a saturation period, a recovery period, $\Delta$, and a CPMG train for detecting the $M_z$ magnetization after recovery time.

Due to the inhomogeneous static field generated by the open geometry of the profile NMR MOUSE, the FID is too short and not detectable. In order to overcome this problem, the most frequently used sequence with single-sided NMR is the CPMG sequence, which consist of a 90° pulse followed by 180° pulses that create a train of spin echoes as shown in FIG. 19. This sequence is essential to refocus, or regain, signal loss due to, the $B_0$ field inhomogeneity. The initial amplitude of the decay can be related to spin density, while the effective relaxation time $T_{2,eff}$ can be extracted by fitting an exponential function to the signal decay. One of skill in the art will recognize that when using a CPMG pulse sequence with a suitable NMR-MOUSE, the appropriate timing of pulses, free evolution periods, and acquisition windows can be essential. To this end, the different components of a suitable CPMG pulse sequence are explained.

The first component of a suitable CPMG pulse sequence is the pulse length (i.e., pl). There are two types of pulses in a CPMG pulse sequence. The initial 90° pulse turns the longitudinal magnetization to a detectable transverse magnetization, while the following train of 180° pulses refocuses the effect of the $B_0$ field inhomogeneity by generating the spin echoes. These two pulses are used with the same pulse length in case of an NMR-MOUSE.

The second component of a suitable CPMG pulse sequence is the echo time (i.e., $2\tau$). The echo time is the delay between two echoes which is determined by the time between different pulses. The delay between 90° and 180° pulses is $\tau$–pl, whereas the delay between consecutive 180° pulses is $2\tau$–pl. The echo signals are acquired in the centre between two consecutive 1800 pulses. In order to achieve the maximum sensitivity, the echo time is preferably as short as possible. However, the minimum echo time is limited by the dead time of the probe and the length of the acquisition window.

The third component of a suitable CPMG pulse sequence is the acquisition time (i.e., acq). The echoes are acquired in the centre between two consecutive scans. For the acquisition, it is very important to set a fast dwell time (i.e. dwell time=1 s with a broad bandwidth=1 MHz) where the dwell time is the delay between consecutive acquired points during one echo. To maximize the detection sensitivity, the acquisition time should be set in a way that the echo is acquired from half-to-half intensity. However, the length of the acquisition window also determines the spatial resolution.

The final component of a suitable CPMG pulse sequence is the number of scans and repetition time. A sufficient signal-to-noise ratio (SNR) can be achieved when the CPMG pulse sequence is repeated several times and the signal of the different scans is averaged to improve signal-to-noise. These scans are separated by a time called the recycle delay (i.e., the "repetition time"). During this time, z-magnetization is recovered, which is needed to perform the next scan. To achieve a maximum recovery of the magnetization, the recycle delay should be at least 5 times the $T_1$ (longitudinal relaxation time). When the repetition time is equal to $5T_1$, 99.32% of the magnetization in Z-direction has come back to its original value. Although only 77.68% of the magnetization has returned after $1.5T_1$, the highest signal-to-noise ratio per time is reached here. But liquid quantification applying $1.5T_1$ is not possible as $T_1$ will be a function of material type and its saturation level.

A process for the analysis and mapping of fluid flow though a sample 34 provided as an absorbent article can be designed to use the device 10, described supra, with using a contrast agent and selecting a repetition time and number of echoes so that the resulting NMR signal is not $T_2$ or $T_1$ weighted and therefore the calculated liquid amount is independent of the materials itself. Without desiring to be bound by theory, it is believed that the quantification of liquid amount present within sample 34 can be material independent when the device 10 is coupled with an optimized CPMG pulse sequence and the use of a specific contrast agent.

One of skill in the art will appreciate that the addition of low concentrations of paramagnetic solutes can drastically shorten the relaxation times. To this end, one of skill in the art will understand that there are two general categories of magnetic contrast agents. The first category consists of paramagnetic ions, complexes, and molecules, and combinations thereof that can create rapidly fluctuating and locally inhomogeneous magnetic fields with frequency components in a range that can cause decreases in both $T_1$ and $T_2$. The second category consists of magnetic particles, such as ferromagnetic powders, that generate locally nearly static magnetic field inhomogeneities that cause a decrease in the transverse relaxation time $T_2$, but not in the longitudinal relaxation time $T_1$.

Contrary to contrast agent prior art teachings, the objective of using a contrast agent in the disclosed process is to make all liquid inside different test materials look the same by decreasing the $T_1$ relaxation time to a level that $T_1$ is independent of material type and its concentration level, and additionally reduce the required repetition time enabling the analysis of fluid redistribution kinetics. In addition, fluids containing the first category of contrast agents still have a long enough $T_2$ time to avoid $T_2$ weighing of the signal as $T_2$ is also a function of saturation level and material type without using contrast agent. Therefore, contrast agents that belong to the first category can be particularly suitable.

A suitable contrast agent preferably has minimal effect on materials and can be mixed homogeneously with the test and/or insult fluids. In other words, the addition of a contrast agent should preferably not change the critical properties of the test and/or insult fluids. In particular, it was surprisingly found that the $Gd^{3+}$ complex (Diethylenetriaminepentaacetic acid gadolinium(III) dihydrogen salt hydrate, 97%) contrast agent dissolves in 0.9% saline solution or paper industrial fluid (PIF) without causing flocculation and changes due to its viscosity. PIF is a highly viscous fluid used to simulate viscous fluids in contact with hygiene products.

Suitable contrast agents can be selected from the group consisting of paramagnetic, super-paramagnetic, protein-based, paramagnetic rare-earth-based, and combinations thereof. Suitable paramagnetic contrast agents can be selected from the group consisting of Gadolinium-based, Manganese-based, Dysprosium-based, Holmium-based, Terbium-based, Erbium-based, and combinations thereof. Suitable super-paramagnetic contrast agents can be selected from the group consisting of Iron Oxide-based, Iron Platinum-based, and combinations thereof. Suitable paramagnetic rare-earth-based contrast agents can be selected from the group consisting of Dysprosium oxide, gadolinium oxide, holmium oxide, erbium oxide, yttrium oxide, ytterbium-oxide, Dysprosium hydroxide, gadolinium hydroxide, holmium hydroxide, erbium hydroxide, yttrium hydroxide, ytterbium-hydroxide, and combinations thereof. Suitable Gadolinium-based ($Gd^{3+}$) contrast agents can be selected from the group consisting of gadoterate, gadodiamide, gadobenate, gadopentetate, gadoteridol, gadoversetamide, gadobutrol, gadopentetic acid dimeglumine, gadofosveset, gadocoletic acid, Polymeric gadolinium complexes such as gadomelitol, and gadomer 17, gadoxetic acid, gadoxetate, and combinations thereof. Suitable Iron oxide-based contrast agents can be selected from the group consisting of oral iron oxide contrast agent, Feridex I.V., Resovist, Sinerem, Lumirem, Clariscan, and combinations thereof. Suitable Iron Platinum-based contrast agents can be selected from the group consisting of superparamagnetic iron platinum particles (SIPPs). Suitable Iron Manganese-based contrast agents can be selected from the group consisting of Mn-DPDP, Manganese ions (Manganese Enhanced MRI), $Mn^{2+}$ carbon nanostructure complexes of graphene oxide nanoplatelets, graphene oxide nanoribbons, and combinations thereof.

NMR Testing Process

The unique procedure outlined infra can facilitate the: a) measurement of a dry sample 34 profile b) kinetic measurement of sample 34, and c) measurement of a wet sample 34 profile. In other words, the described process can facilitate the measurement of the kinetics and liquid distribution inside a sample 34 (e.g., a hygiene product) quantitatively within very short time.

By way of non-limiting example, samples 34 are conditioned at 23° C.±2° C. and about 50%±2% relative humidity for twelve (12) hours prior to testing. A sample 34 (e.g., an absorbent article such as a diaper and/or catamenial) is prepared by placing the sample 34 flat onto a lab bench and identifying the intersection of the longitudinal and lateral centerlines of the sample 34. For a sample 34 provided as a pant product, any cuffs or waistbands are removed taking care not to damage the top sheet or absorbent body of the sample 34. The sample 34 or article can be attached to the front 40 and back 42 sample supports of secondary frame 36 by attachment means 44. Attachment means 44 can be provided as either adhesive tape or mechanical "hook" fasteners with the top sheet of sample 44 facing upward (i.e., the absorbent article 34 is positioned so that the top sheet of the absorbent article is disposed proximate to NMR sensor 16).

Preferably, sample 34 is placed in a manner so that just the chassis and not the absorptive core of sample 34 overlays secondary frame 36. The front 40 and back 42 sample supports are attached to the secondary frame 36 so that the absorbent article will be centered longitudinally and laterally relative to insult application aperture 50 when the top plate assembly 20 has been closed relative to bladder assembly 18. The back end of the sample 34 is secured to back 42 sample support of secondary frame 36 by either adhesive tape or mechanical "hook" fasteners, once again ensuring that only the chassis and not the absorptive core overlays the application aperture 50. The back sample support 42 is then attached to the secondary frame 36 so that the sample 34 is taut but not stretched. The top plate assembly 20 is closed and fastenably attached to bladder assembly 18 to form pressure chamber 14. The bladder of pressure chamber 14 is inflated up to 30 psi.

In other words, preparation of the sample 34 for analysis by the device 10 incorporating NMR sensor 16 can be summarized as follows:

1. Prepare the sample 34 (e.g., remove/cut the cuffs, determine loading point, determine wetting conditions, etc.).
2. Move the NMR sensor 16 away from the insult application aperture 50 disposed within top plate assembly 20 relative to a position disposed distal from insult application aperture 50.
3. Open the glass cover by disassociating top plate assembly 20 of pressure chamber 14 from bladder assembly 18.
4. Insert the sample 34 (e.g., diaper and/or catamenial device) by attaching the sample 34 to front sample support 40 and back sample support 42 to anchor a sample 34 or article to be measured by the device 10 relative to bladder assembly 18 by attachment means 44.
5. Close top plate assembly 20 by cooperatively associating top plate assembly 20 of pressure chamber 14 to bladder assembly 18.
6. Apply and regulate the pressure applied to bladder 32 disposed within bladder assembly 18 disposed within pressure chamber 14 to the desired value.

Figure 21:
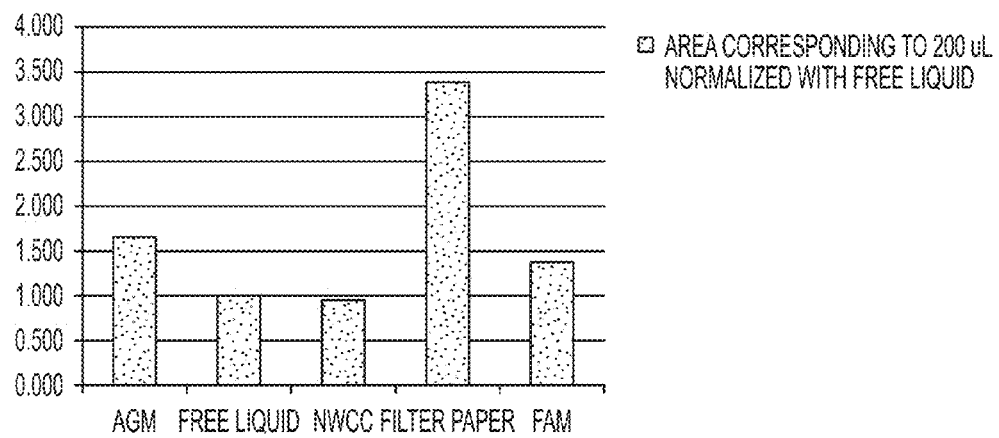
FIG. 21 is a graphical representation of the calculated liquid amount disposed within an absorbent article where the liquid does not have a contrast agent disposed therein showing fluid amounts are independent of the materials comprising sample 34 itself.
Figure 22:
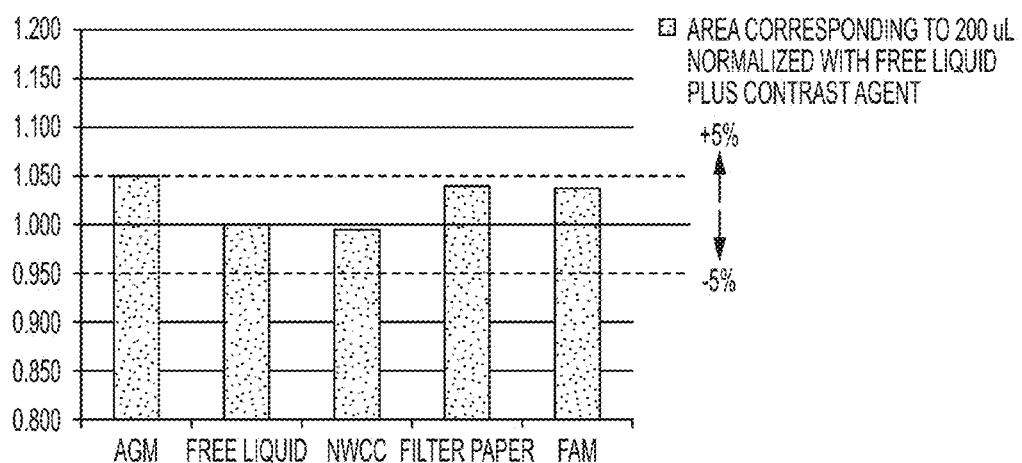
FIG. 22 is a graphical representation of the quantification of liquid amount present within a sample provided as an absorbent article showing that fluid quantification can be material independent when the device is coupled with an optimized CPMG pulse sequence and the use of a contrast agent.

Preferably, the process for the analysis and mapping of fluid flow (presented as an insult) though a sample 34 (provided as an absorbent article) can be designed to use the device 10, described supra, along with a $Gd^{3+}$ contrast agent and tuning the repetition time so that the resulting NMR signal is not $T_2$ or $T_1$ weighted. Therefore, the calculated liquid amount is independent of the materials, or layers of materials, comprising sample 34 itself. As shown in FIG. 21 for example, and without desiring to be bound by theory, it is believed that not using a contrast agent provides a material dependence in liquid quantification within sample 34 provided as an absorbent article. As shown in FIG. 22 conversely, without desiring to be bound by theory, it is believed that the quantification of liquid amount present within sample 34 provided as an absorbent article can be material independent when the device 10 is coupled with an optimized CPMG pulse sequence and the use of a contrast agent. Additionally, and as discussed supra, the device 10 can allow for the measurement of the insult distribution in the x-, y-, and/or z-axis and as a function of the inclined absorbent article 34 (i.e., the overall curvature of the absorbent article 34).

In principle, the exemplary process for the analysis and mapping of fluid flow though a sample 34 is based on wetting of the examined hygiene product with series of liquid insults of the given flow parameters and evaluating fluid distribution inside the absorbent article 34. The equipment is capable of two different experimental possibilities (i.e., real time kinetics and profiling in equilibrium state). Due to application of pressure to the bottom of the absorbent article 34, absorbent article 34 swelling is directed away from NMR sensor 16. Therefore, distance between the absorbent article 34 surface and the NMR sensor 16 is always kept constant and does not change with different experimental conditions.

Kinetic Testing Process

Figure 23:
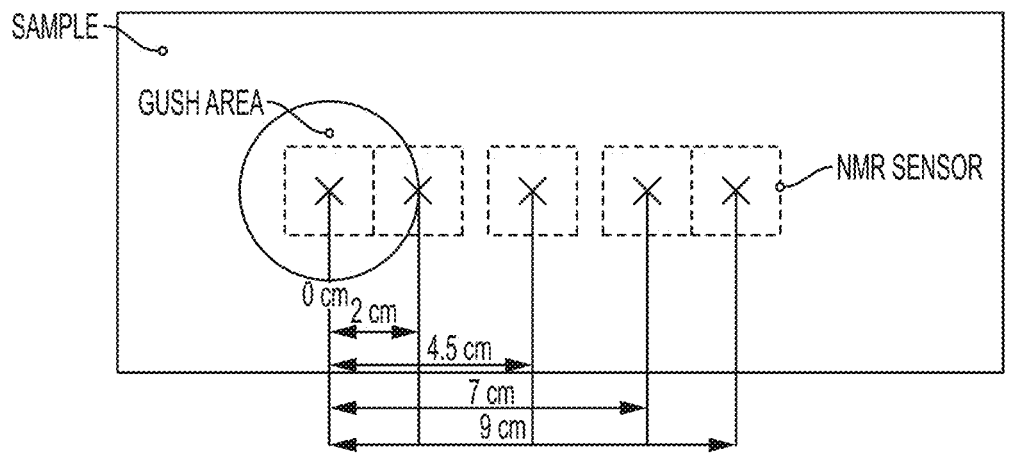
FIG. 23 is a plan view of an exemplary plan of NMR sensor positions from the insult/gush center relative to the insult application aperture and at given height from the sample surface.

By way of non-limiting example, the kinetic testing process focuses on dynamic performance of the materials comprising sample 34 when an insult is applied via deposition assembly 22 through insult application aperture 50 onto the top sheet of sample 34 disposed within pressure assembly 14. Typically, 4 gushes of insult are used with 5 min breaks in between consecutive insults. Since performance of the topsheet is of main interest, a kinetic measurement can generally consider only the outermost part of the sample 34. As shown in FIG. 23, when measurements of an insulted sample 34 are conducted, the NMR sensor 16 is preferably positioned a known distance from the insult/gush center relative to insult application aperture 50 and at given height from the sample 34 surface. The kinetic measurement then provides for the acquisition of a resulting NMR signal in response to the wetting action of the applied insults/gushes.

It was found that the use of the optimized CPMG pulse sequence in combination of the use of a contrast agent enables the quantitative measurement of liquid inside hygiene products and materials. Linearity of $r^2 > 0.99$ has been achieved at very fast scans 1-5 Hz per NMR experiment.

In other words, the process for conducting the kinetic testing process of the sample 34 for analysis by the device 10 incorporating NMR sensor 16 can be summarized as follows:
1. Position NMR sensor 16 proximate to insult application aperture 50 disposed within top plate assembly 20 horizontally and proximate to insult/gush area; position the NMR sensor 16 as required from the geographic center of the insult/gush center.
2. Position NMR sensor 16 1400 μm from the top surface of sample 34 contactingly engaged with top plate assembly 20 of bladder assembly 18.
3. Dispose insult fluid and contrast agent within deposition assembly 22.
4. Position deposition assembly 22 relative to insult application aperture 50 and the top surface of sample 34.
5. Insult top surface of sample 34 with at least a portion of insult fluid and contrast agent through deposition assembly 22.
6. Initiate kinetic measurement with NMR sensor 16.
7. Apply series of insult/gushes with the predefined parameters (e.g., 4 injections of 40 mL, flow rate 10 mL/sec, 5 min break between the gushes).
8. Complete measurements.

Profile Testing Process

By way of non-limiting example, regarding to the fact that overall time necessary to perform a kinetic measurement is sufficient for wetting liquid (i.e., the insult to be applied) to reach equilibrium, profiling testing may be started immediately after a kinetic evaluation. Profiling gives signal response versus sample depth and it aims to screen the sample within the given measurement range (1.5 mm for the current setup, will be improved in the future). This way liquid distribution across different sample layers can be quantified. Profiling is conducted in different spots along the sample length (differentiation along increasing distance from the gush center), 2-D liquid distribution inside the sample can be finally obtained by combining the obtained results. An exemplary schematic top view for 5 profiling spots (x) used in the study is shown in FIG. 23. Note that a distance of 9 cm for profiling is the same position as the sensor is placed in case of kinetics measurements.

In other words, the process for conducting the profile testing process of the sample 34 for analysis by the device 10 incorporating NMR sensor 16 can be summarized as follows:
1. Translate the NMR sensor 16 to its top position distal from sample 34 disposed within bladder assembly 18, reaching an outermost vertical position.
2. Move the NMR sensor 16 to an outermost horizontal position disposed distal from insult application aperture 50.
3. Remove the deposition assembly 22 from contacting engagement with insult application aperture 50.
4. Move the NMR sensor 16 horizontally (i.e., y-direction) relative to insult application aperture 50 so NMR sensor 16 center overlaps insult application aperture 50 center (i.e., position 0 cm).
5. Run profiling experiment (scanning range 0-1700 m, step size 50 μm).
6. Set the NMR sensor 16 to an initial position (1700 μm) relative to the top of sample 34 disposed within bladder assembly 18 and lower its position incrementally 50 μm as required.
7. When the experiment is completed, translate the NMR sensor 16 to the outermost vertical (i.e., Z-direction) position.
8. Repeat steps 4-7 while placing the sensor at positions 2, 4.5, 7 and 9 cm from the insult/gush center.

Figure 24:
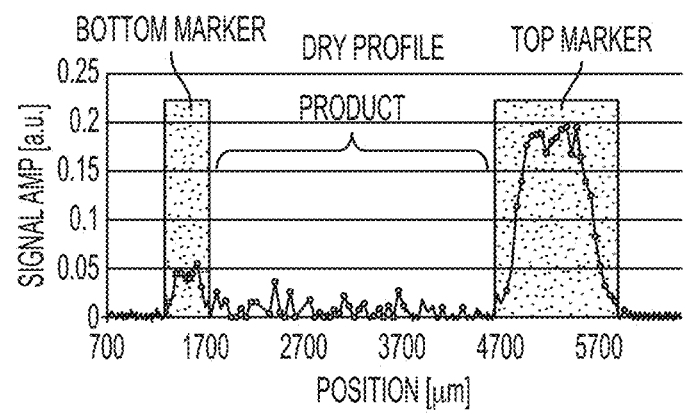
FIG. 24 is an exemplary graphic of the liquid distribution as a function of product depth in the Z-direction for a dry sample 34.
Figure 25:
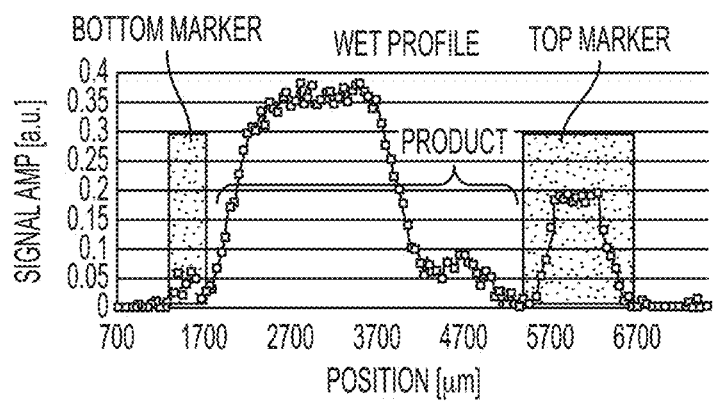
FIG. 25 is an exemplary graphic of the liquid distribution as a function of product depth in the Z-direction for a wet sample.

The liquid distribution as a function of product depth in the Z-direction can be represented graphically as shown in FIGS. 24-25. For example, an exemplary liquid distribution as a function of product depth in the Z-direction for a dry sample 34 could be graphically presented as shown in FIG. 24. An exemplary liquid distribution as a function of product depth in the Z-direction for a wet sample 34 could be graphically presented as shown in FIG. 25.

Figure 26:
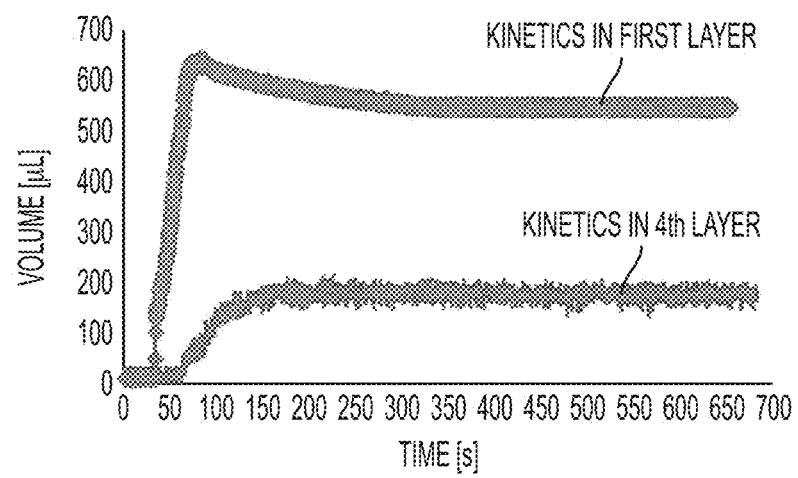
FIG. 26 is an exemplary graphic showing the liquid amount at a known position within sample as a function of time.

As shown in FIG. 26, an exemplary liquid amount at a known position within sample 34 as a function of time can be measured within the sensitive NMR volume and can be graphically represented as shown. The exemplary relationship between liquid amount and known position of FIG. 26 is shown with a sample 34 provided as a plurality of stacked filter paper (i.e., 4 filter papers).

At the conclusion of testing, the sample 34 can be extricated from the device 10 as follows:
1. Translate NMR sensor 16 vertically (i.e., Z-direction) to an outermost position.
2. Translate NMR sensor 16 horizontally (i.e., y-direction) to an outermost horizontal position.
3. Release pressure applied to bladder 32.
4. Disassociate top plate assembly 20 of pressure chamber 14 from bladder assembly 18.
5. Remove the sample 34 from pressure chamber 14.
6. Close top plate assembly 20 by cooperatively associating top plate assembly 20 of pressure chamber 14 to bladder assembly 18.

It should be noted that with the regular NMR-MOUSE the distance between the RF Coil of the NMR sensor 16 and the top layer of the sample 34 disposed within bladder assembly 18 may not be constant during the absorptive process due to swelling of the sample 34. Use of the bladder assembly 18 in conjunction with NMR sensor 16 provided as device 10 was surprisingly found to provide a measurement by NMR sensor 16 independent of any swelling experienced by sample 34 as the sample 34 can swell away from the sensitive slice currently being scanned by NMR sensor 16.

EXAMPLES

As will be recognized by one of skill in the art, the process provided herein can be used for a relative comparison of the performance of absorbent articles provided as sample 34. For example absorbent articles provided as sample 34 can be provided as diapers where a user seeks to determine diaper topsheet dryness.

An exemplary investigation comprised a plurality of diaper products. The experiments were conducted on 4 different baby diaper products, for example products A, B, C, and D.

Figure 27:
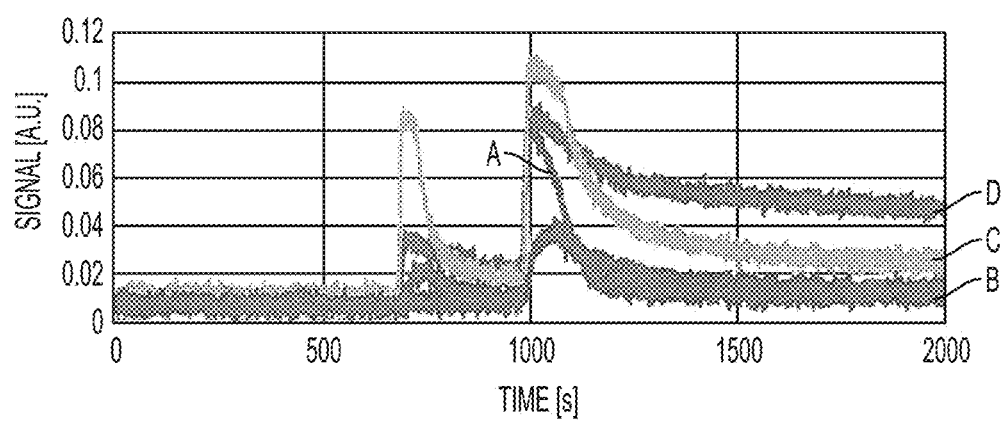
FIG. 27 is an exemplary graphic representation of relative signal vs. time detection between the $3^{rd}$ and $4^{th}$ gushes from a plurality of insults presented to different representative samples using the Kinetic Testing Process.

After conducting the Kinetic Testing Process described supra, the third and fourth gushes from a plurality of insults presented to each respective sample 34 were detected (i.e., peaks corresponding to ~700 and ~1000 s respectively). The relative signal (or liquid volume) versus time is graphically represented in FIG. 27 for each sample 34. As can be seen there are distinctive disparities in performance between all sample products 34. The graphical representation also depicts the respective recovery rates after the particular gushes.

Among the samples presented, product D transported the liquid insult through the top sheet of the absorbent article the fastest as indicated by low second and third signal peaks. As can be seen conversely, product C kept the topsheet surface dry. As absorption of the insult by a diaper can be driven by the competition between liquid spreading in both vertical (Z-direction) and horizontal (y-direction) directions, the liquid may not reach 9 cm distance with the initial volumes applied for the sample 34 wetting. By moving the NMR sensor 16 closer to the gush area, any initial gushes can be detected.

Figure 28:
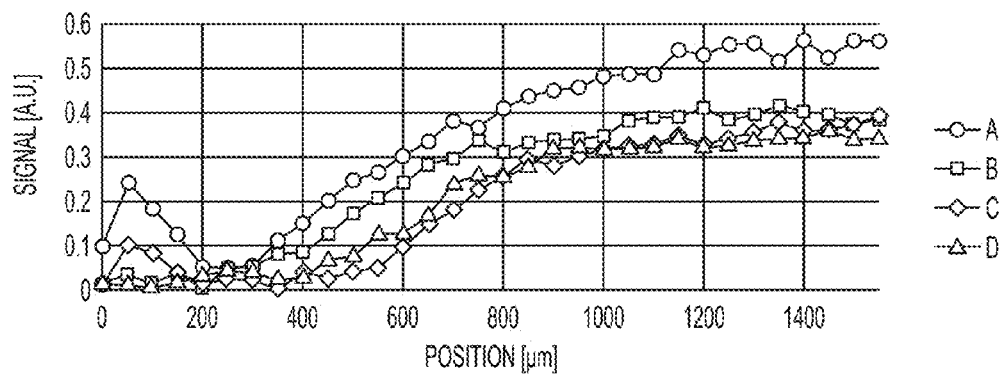
FIG. 28 is an exemplary graphic showing profile results of the liquid distribution within the particular layers for representative products.

FIG. 28 provides the profile results of the liquid distribution within the particular sample layers. As represented by the graphic of FIG. 28, the sample 34 profiles at the 9 cm position indicate that the biggest liquid accumulation in the top sheet of each respective sample 34 (0-200 μm depth) appears in case of A, while the smallest over the C and D top layers.

Figure 29:
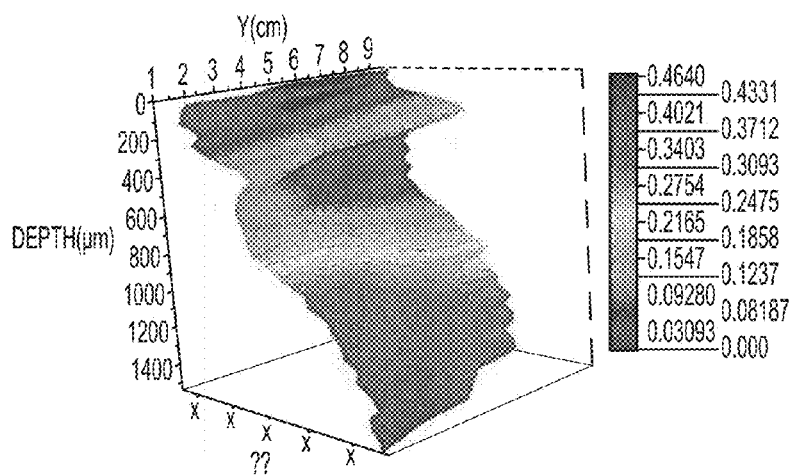
FIG. 29 is an exemplary 2-D graphic representation of the liquid distributions in exemplary sample A.
Figure 30:
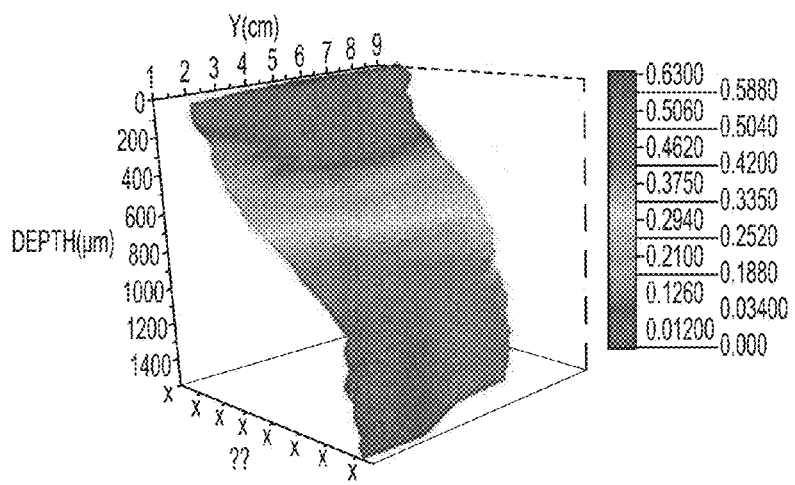
FIG. 30 is an exemplary 2-D graphic representation of the liquid distributions in exemplary sample B.
Figure 31:
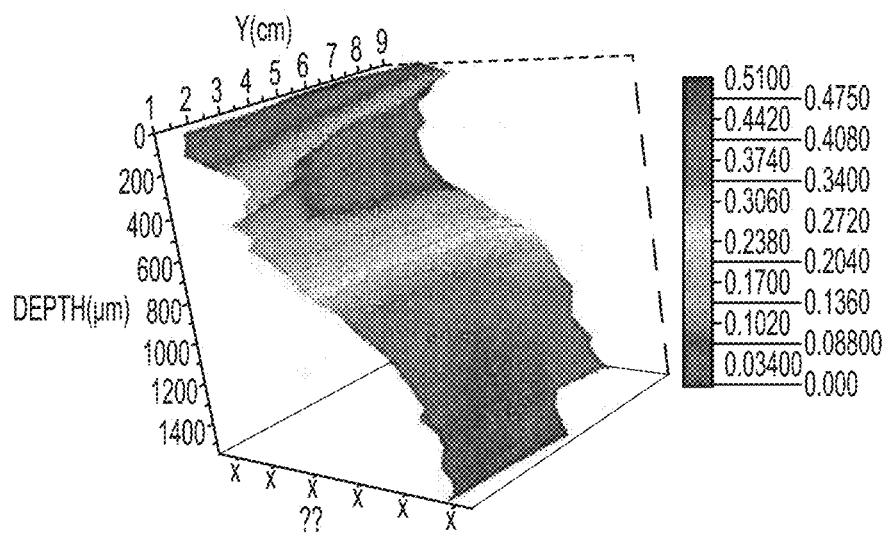
FIG. 31 is an exemplary 2-D graphic representation of the liquid distributions in exemplary sample C; and, FIG. 32 is an exemplary 2-D graphic representation of the liquid distributions in exemplary sample D.
Figure 32:
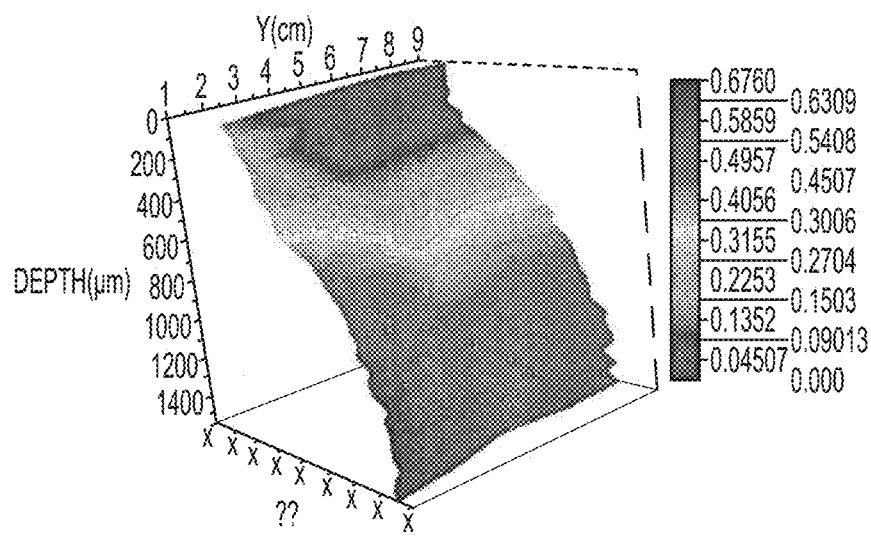

By combining the profiling results for different spots (0, 2, 4.5, 7, 9 cm from the gush center) for each of the diaper case, an exemplary 2-D liquid distribution mapping can be obtained. FIGS. 29-32 present exemplary 2-D graphic representations of the liquid distributions in each of the respective samples 34. FIG. 29 presents an exemplary 2-D graphic representation of the liquid distributions in product A. FIG. 30 presents an exemplary 2-D graphic representation of the liquid distributions in product B. FIG. 31 presents an exemplary 2-D graphic representation of the liquid distributions in product C. Finally, FIG. 32 presents an exemplary 2-D graphic representation of the liquid distributions in product D. As observed in FIGS. 29 and 32, differences between product A and product D regarding dryness of the top layer can be observed. As observed in FIGS. 30 and 32, after reaching equilibrium, almost no liquid accumulation was observed in case of product C and product D. As observed in FIGS. 29 and 31, the top sheet stored liquid.

One of skill in the art will recognize that the processes described herein can further comprise full automation of any portion of the data collection system and any or all ensuing data analysis. In any regard, the methods described herein can be a key testing procedure for absorbent articles that can assist to drive claim support for top sheet materials as well as model and product development.

All publications, patent applications, and issued patents mentioned herein are hereby incorporated in their entirety by reference. Citation of any reference is not an admission regarding any determination as to its availability as prior art to the claimed invention.

The dimensions and/or values disclosed herein are not to be understood as being strictly limited to the exact numerical values recited. Instead, unless otherwise specified, each such dimension and/or value is intended to mean both the recited dimension and/or value and a functionally equivalent range surrounding that dimension and/or value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for quantitatively profiling fluid distribution in multi-layer absorbent articles, the process comprising the steps of:
   a) providing a device comprising a frame, a pressure chamber, and an NMR sensor, said pressure chamber comprising a conformable surface and a top plate disposed adjacent thereto, said conformable surface and said top plate being separable;
   b) providing a first multi-layer absorbent article, said first multi-layer absorbent article having a top sheet and an absorbent core, said top sheet and said absorbent core comprising nuclei having excitable nuclear spins excited by radiofrequency pulses emitted by said NMR sensor;
   c) positioning said first multi-layer absorbent article between said conformable surface and said top plate, said top sheet of said first multi-layer absorbent article being disposed within said pressure chamber so said absorbent core is disposed proximate to and in contacting engagement with said conformable surface and said top sheet is disposed proximate to and in contacting engagement with said top plate when said conformable surface and said top plate of said pressure chamber are conjoined;
   d) disposing said NMR sensor at a first position relative to said top plate and said top sheet contactingly engaged thereto;
   e) emitting said radiofrequency pulses from said NMR sensor to define a float sensitive volume of said first multi-layer absorbent article at said first position;
   f) detecting at least a portion of said nuclei having a non-zero spin interacting with said radiofrequency pulses at said first position; and,
   g) producing said fluid distribution profile of said first multi-layer absorbent article according to said detected nuclei having a non-zero spin interacting with said radiofrequency pulses at said first position, h) wherein said top plate comprises an insult application aperture, said insult application aperture being disposed within said top plate and facilitating contacting engagement of at least a first fluid to said top sheet through said top plate.

2. The process of claim 1 further comprising the step of insulting said top sheet of said first multi-layer absorbent article with at least a first fluid.

3. The process of claim 1 further comprising the step of providing said first fluid with a contrast agent.

4. The process of claim 3 further comprising the step of selecting said contrast agent from the group consisting of paramagnetic contrast agents, super-paramagnetic contrast agents, protein-based contrast agents, paramagnetic rare-earth-based contrast agents, and combinations thereof.

5. The process of claim 4 further comprising the step of selecting said contrast agents from the group consisting of Gadolinium-based contrast agents, Manganese-based contrast agents, Dysprosium-based contrast agents, Holmium-based contrast agents, Terbium-based contrast agents, Erbium-based contrast agents, Iron Oxide-based contrast agents, Iron Platinum-based contrast agents, Dysprosium oxide contrast agents, gadolinium oxide contrast agents, holmium oxide contrast agents, erbium oxide contrast agents, yttrium oxide contrast agents, ytterbium-oxide contrast agents, Dysprosium hydroxide contrast agents, gadolinium hydroxide contrast agents, holmium hydroxide contrast agents, erbium hydroxide contrast agents, yttrium hydroxide contrast agents, ytterbium-hydroxide contrast agents, gadoterate, gadodiamide, gadobenate, gadopentetate, gadoteridol, gadoversetamide, gadobutrol, gadopentetic acid dimeglumine, gadofosveset, gadocoletic acid, gadomelitol, gadomer 17, gadoxetic acid, gadoxetate, oral iron oxide, Feridex I.V., Resovist, Sinerem, Lumirem, Clariscan, superparamagnetic iron platinum particles (SIPPs), Mn-DPDP, Manganese ions (Manganese Enhanced MRI), $Mn^{2+}$ carbon nanostructure complexes of graphene oxide nanoplatelets, graphene oxide nanoribbons, and combinations thereof.

6. The process of claim 1 further comprising the step of providing a deposition assembly said deposition assembly being capable of at least containing said at least a first fluid and disposing said at least a first fluid upon said top sheet through said insult application aperture disposed within said top plate.

7. The process of claim 1 wherein said step of emitting radiofrequency pulses from said NMR sensor further comprises the step of emitting a CPMG pulse sequence from said NMR sensor.

8. The process of claim 7 wherein said step of emitting a CPMG pulse sequence from said NMR sensor further comprises the step of emitting a CPMG pulse sequence from said NMR sensor having echo time, Te, <100 µs, Number of Echoes, NE, <128, and a repetition time <1 sec.

9. The process of claim 1 wherein said step c) further comprises the steps of securing said first multi-layer absorbent article to a flange and securing said flange to said conformable surface.

10. The process of claim 1 further comprising the step of providing said conformable surface with a bladder, said first multi-layer absorbent article being disposed between said bladder and said top plate.

11. The process of claim 10 further comprising the step of applying a pressure to said bladder, said pressure applied to said bladder applying a pressure to said absorbent core and said top plate contactingly engaged to said topsheet thereof.

12. The process of claim 11 wherein said step of applying said pressure to said bladder further comprises the step of applying a pressure of about 0.1 PSI to about 2.0 PSI.

13. The process of claim 1 further comprising the steps of, in place of said step g) providing the steps of:
   i) translating said NMR sensor relative to said first multi-layer absorbent article and said first position to a second position relative to said top plate and said top sheet contactingly engaged thereto;
   j) emitting additional radiofrequency pulses from said NMR sensor to define a second float sensitive volume of said first multi-layer absorbent article at said second position;
   k) detecting at least a portion of said nuclei having a non-zero spin interacting with said radiofrequency pulses at said second position;
   l) producing said fluid distribution profile of said first multi-layer absorbent article by comparing said detected nuclei having a non-zero spin interacting with said radiofrequency pulses at said first position and said detected nuclei having a non-zero spin interacting with said radiofrequency pulses at said second position.

14. The process of claim 13 wherein said step h) further comprises the steps of defining a Z-direction relative to said first multi-layer absorbent article and translating said NMR sensor relative to said first multi-layer absorbent article in said Z-direction.

15. The process of claim 13 wherein said step h) further comprises the steps of defining a y-direction relative to said first multi-layer absorbent article and translating said NMR sensor relative to said first multi-layer absorbent article in said y-direction.

16. The process of claim 13 wherein said step h) further comprises the steps of defining a Z-direction relative to said first multi-layer absorbent article, defining a y-direction relative to said first multi-layer absorbent article, and translating said NMR sensor relative to said first multi-layer absorbent article in at least one of said Z- and y-directions.

17. The process of claim 1 further comprising the step of, prior to said step d), translating said pressure chamber, said first multi-layer absorbent article, and said NMR sensor relative to said frame.

* * * * *